(12) United States Patent
Bechler et al.

(10) Patent No.: US 8,523,754 B2
(45) Date of Patent: Sep. 3, 2013

(54) MULTI-POLAR MAGNETIC DEVICES FOR TREATING PATIENTS AND METHODS THEREFOR

(76) Inventors: Laurie A. Bechler, Asbury, NJ (US); Joseph R. Mele, Bridgewater, NJ (US)

( * ) Notice: Subject to any disclaimer, the term of this patent is extended or adjusted under 35 U.S.C. 154(b) by 455 days.

(21) Appl. No.: 12/916,229

(22) Filed: Oct. 29, 2010

(65) Prior Publication Data

US 2012/0108884 A1    May 3, 2012

(51) Int. Cl.
*A61N 1/00* (2006.01)

(52) U.S. Cl.
USPC .......................................................... 600/15

(58) Field of Classification Search
USPC ...................................................... 600/9–15
See application file for complete search history.

(56) References Cited

U.S. PATENT DOCUMENTS

| | | | |
|---|---|---|---|
| 272,904 | A | 2/1883 | Russell |
| 1,551,229 | A | 8/1925 | Araya |
| 3,921,620 | A | 11/1975 | Nakayama |
| 3,943,912 | A | 3/1976 | Nakayama |
| 4,162,672 | A | 7/1979 | Yazaki |
| 4,232,680 | A | 11/1980 | Hudleson et al. |
| 4,233,965 | A | 11/1980 | Fairbanks |
| 4,330,892 | A | 5/1982 | Fukushima |
| 4,431,002 | A | 2/1984 | Maurer et al. |
| 4,454,883 | A | 6/1984 | Fellus |
| 4,480,596 | A | 11/1984 | Shumiyashu |
| 4,489,711 | A | 12/1984 | Latzke |
| 4,489,711 | B1 | 12/1984 | Latzke |
| 4,509,219 | A | 4/1985 | Yagi |
| 4,549,532 | A | 10/1985 | Baermann |
| 4,549,532 | B1 | 10/1985 | Baermann |
| 4,556,051 | A | 12/1985 | Maurer |
| 4,587,956 | A | 5/1986 | Griffin et al. |
| 5,188,107 | A | 2/1993 | Omura |
| 5,226,020 | A * | 7/1993 | Li et al. ............................ 368/10 |
| 5,312,321 | A * | 5/1994 | Holcomb .......................... 600/9 |
| 5,855,539 | A | 1/1999 | Wise |
| 5,941,902 | A | 8/1999 | Holcomb |
| 5,965,282 | A * | 10/1999 | Baermann ..................... 428/800 |
| 6,113,530 | A * | 9/2000 | Chien ............................... 600/9 |
| 6,205,356 | B1 | 3/2001 | Holcomb |
| 6,280,376 | B1 * | 8/2001 | Holcomb ......................... 600/13 |
| 6,741,889 | B1 | 5/2004 | Holcomb |
| 6,776,753 | B1 | 8/2004 | Holcomb |
| 6,932,889 | B1 | 8/2005 | Holcomb |
| 6,991,594 | B2 | 1/2006 | Holcomb |
| 7,632,226 | B2 * | 12/2009 | Lee ................................. 600/15 |

FOREIGN PATENT DOCUMENTS

| | | |
|---|---|---|
| EP | 0428474 | 5/1991 |
| GB | 1479734 | 7/1977 |
| GB | 2196855 | 5/1988 |
| WO | 9115263 | 10/1991 |

* cited by examiner

*Primary Examiner* — John Lacyk

(74) *Attorney, Agent, or Firm* — Doherty & Charney LLC

(57) ABSTRACT

A system for treating patients includes a first magnetic device including a set of four magnetic discs arranged in a square array, the four magnetic discs including two having negative magnetic poles lying in a first plane and two having positive magnetic poles lying in the first plane, wherein the two magnetic discs having negative magnetic poles extend along a first diagonal line and the two magnetic discs having positive magnetic poles extend along a second diagonal line that crosses the first diagonal line, and a housing containing the four magnetic discs for maintaining the magnetic discs in the square array arrangement, the housing including an alignment marker for aligning the first magnetic device on a patient.

15 Claims, 26 Drawing Sheets

FIG. 3
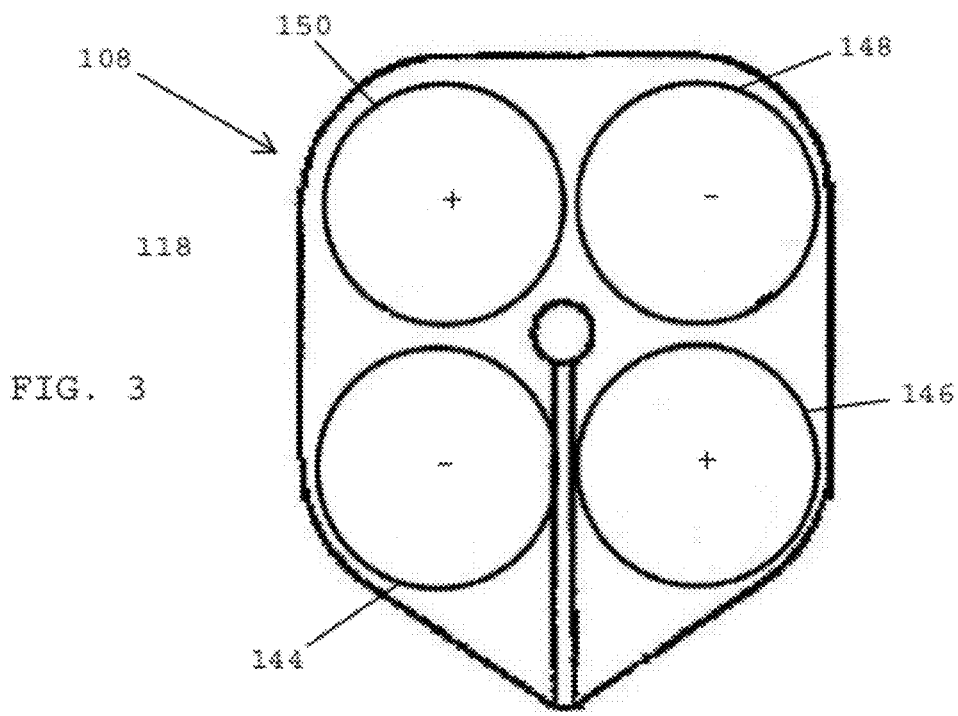
FIG. 4
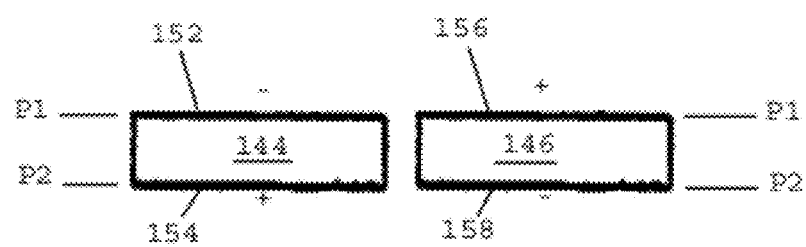
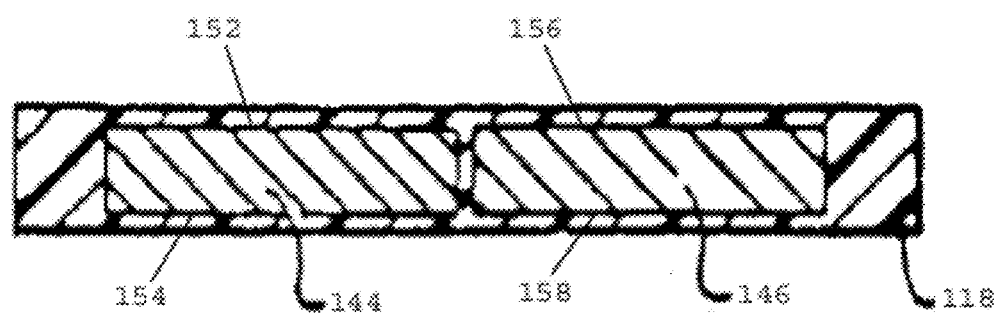
FIG. 5

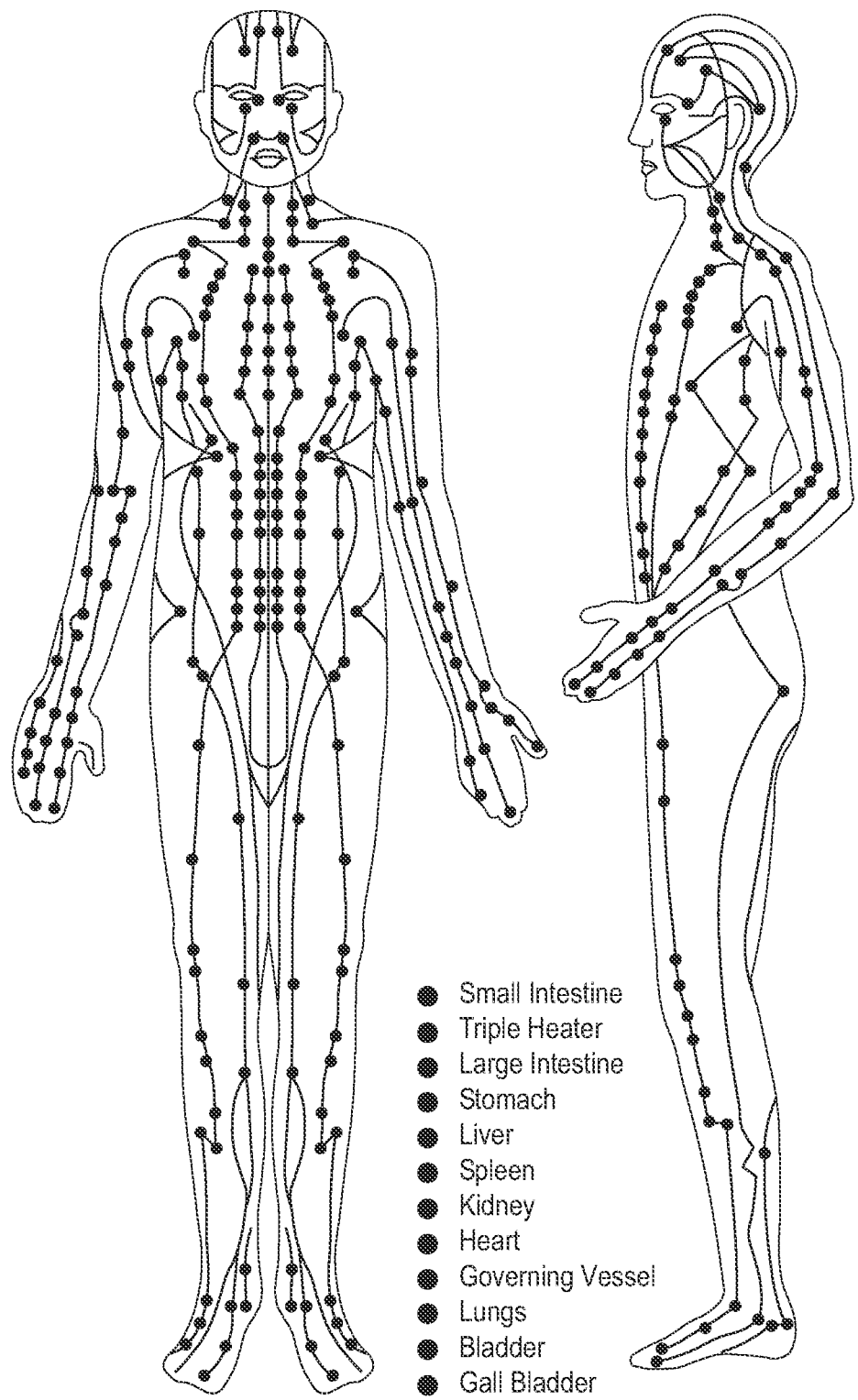
FIG. 7 The Main Meridian Channels

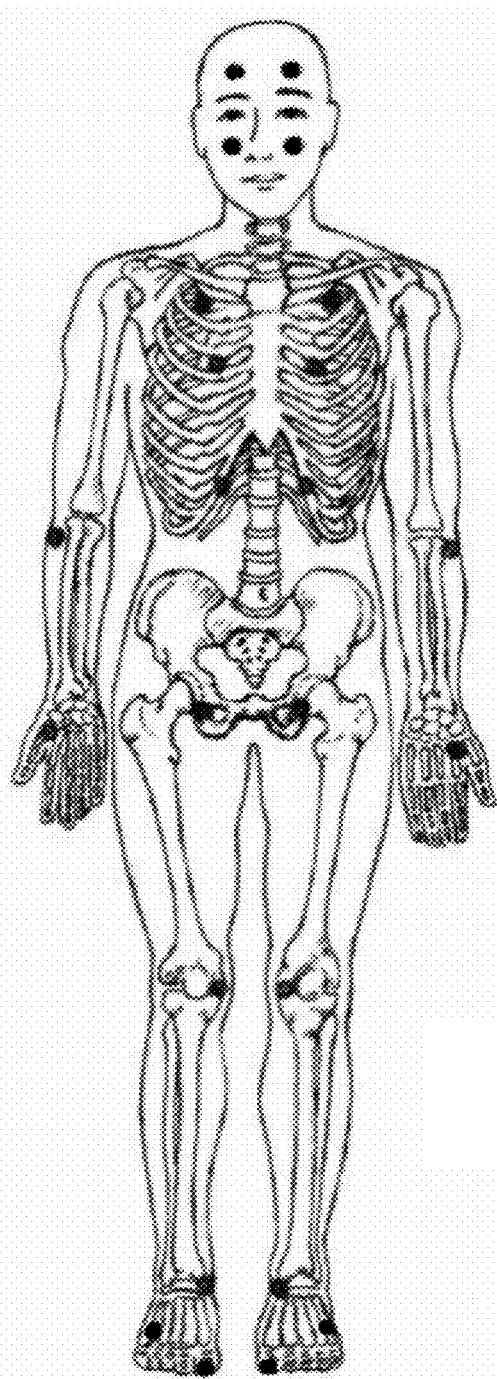
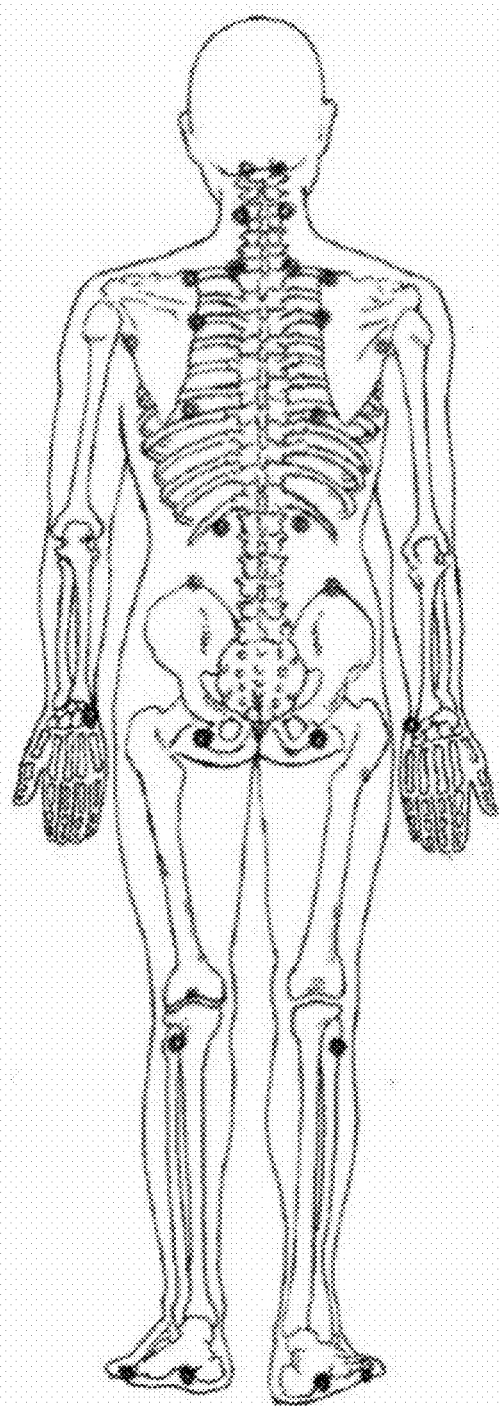
FIG. 8A                    FIG. 8B

MULTI-POLAR MAGNETIC DEVICES FOR TREATING PATIENTS AND METHODS THEREFOR

BACKGROUND OF THE INVENTION

1. Field of the Invention

The present invention generally relates to treating patients for health issues, and more specifically relates to systems, devices and methods that use muscle response testing and multi-polar magnetic devices for treating patients for health issues.

2. Description of the Related Art

For centuries, particular locations on the body, referred to as acupuncture or acupressure points, have been used to aid the body in healing. Each of the points on a human body correlates to a particular electromagnetic line, meridian or "flow" that runs through the body. Hieroglyphics and pictographs from the Shang Dynasty, circa 1600-1100 B.C., suggest that acupuncture was in use during that time period. Chinese documents from the beginning of the first century contain the earliest written record of acupuncture points.

The mummified remains of Ötzi, an iceman estimated to be 5,300 years old, had tattoos on various locations of his body that correlate to acupuncture and meridian points. DNA evidence suggests that Ötzi had genetic markers associated with reduced fertility. It was also found that Ötzi had whipworm, an intestinal parasite, which would have caused him to have abdominal complaints. Ötzi was also found to be suffering from arthritis. Among the tattoos found on his body, the tattoo behind his left knee is the location used today for individuals suffering from abdominal complaints, reproductive organ complaints, and vertigo, to name a few. The tattoo located on the inside of his ankle is used for improving digestion. In addition, his fingernails indicated that he had been sick three times in the six months prior to his death (cause of death was a wound), the last time lasting about two weeks. One of the tattoos is at an area of rejuvenation for the body. The placement of tattoos on Ötzi's body fits his scientifically discovered medical history perfectly, and in fact, if Ötzi went to a practitioner today, there is a good chance that those very same acupuncture points would be chosen to treat his ailments.

The use of acupuncture and acupressure has a more recent history as well. In 1683, a Dutch physician named Willem Ten Rhijne studied acupuncture for two years in Japan, and he mentioned it in an essay he wrote in a medical text on arthritis.

In 1943, Dr. Reinhold Voll, a medical doctor in Germany, was diagnosed with bladder cancer. Western medicine provided him with no hope of a cure so he tried acupuncture and was able to completely heal himself. This experience started his quest to learn more about acupuncture. During his studies of acupuncture, he learned that the points used on the body for acupuncture were in fact more conductive of electricity than the tissue surrounding it. From this discovery he was able to develop the EAV Device (Electromagnetic Acupuncture according to Voll), which is a diagnostic machine that is still widely used today. It is believed that the extra conductivity at or around the acupuncture points is what makes the placement of therapeutic devices at these locations so effective in the treatment of health issues.

Today, acupuncture and other healing arts, such as Jin Shin Jyutsu®, are widely accepted. Medical acupuncture is taught in Harvard Medical School and the Helms Medical Institute, as well as at other well-respected medical schools. Acupuncture, Jin Shin Jyutsu, as well as other similar therapeutic techniques based on traditional Chinese medicine (TCM) have been implemented in many hospitals to help with pain and healing. Although not always fully understood in the West, the value of these ancient healing arts is finally being appreciated by Western medicine.

Magnetism has been used for centuries for healing health complaints, and is possibly even older than acupuncture. Magnetic energy influences every cell in the body. If the cells become depolarized, it has been observed that an individual will tire. Thousands of years ago, the Eastern belief was that the life force or Chi is generated by the Earth's magnetic field. Its use is recorded in ancient Egyptian writings and it is known that Cleopatra wore magnetic jewelry (i.e., a lodestone) on her head in the belief that it would help her maintain a youthful appearance.

The existence of electromagnetic energy and its effect on the human body is being studied more and more in Western medicine. Many prestigious institutions have made it a focal point of clinical trials with such research being conducted at Harvard Medical School, Vanderbilt University Medical Center, and the University of Texas Medical Branch. Today magnetic therapies are accepted and used in many countries.

In 1964, Dr. George J. Goodheart, a doctor of chiropractic medicine, realized that basic chiropractic adjustments were not providing complete and long-term relief for patients' physical complaints. In response, Dr. Goodheart combined the knowledge of those before him with his own experiences involving the muscles of the body in relation to acupuncture therapy to create Applied Kinesiology, a unique method of balancing the electromagnetic lines or flows that run throughout the body. Applied Kinesiology describes a branch of holistic medicine that studies the relationship between muscle movement and the health of the human body.

He achieved significant results using his new methods and found a very important and specific relationship between the muscles and the rest of the body. He later discovered a diagnostic and treatment tool that he called therapy localization. He observed that if a patient touched a part of the body where there was a problem or "blockage," a weak muscle would become strong. From that observation, Dr. Goodheart realized he could use a muscle that was strong and go to various points on the body to detect a reflex or organ that created weakness. This weakness would show up in the muscle that was being tested. In this way problem areas could be identified and solutions could be found. For example, he discovered that if an individual was exposed to supplements that could help a patient, that the physical exposure of the individual to the correct supplement would make a weak muscle strong again.

There are many references that describe the underlying principals of Applied Kinesiology including "Applied Kinesiology," written by Tom and Carole Valentine of Rochester, VT (1985); "Your Body Doesn't Lie," written by John Diamond of New York, NY (1980); and "Thorsons Introductory Guide to Kinesiology—Touch for Health," written by Maggie La Tourelle and Anthea Courtenay of London, England (1992).

Building upon the efforts of Dr. Goodheart and Applied Kinesiology, there is a growing body of medical evidence that indicates that many health issues, whether physical, mental or emotional, are rooted in the electromagnetic lines or flows of the body. Different flows feed different sections of the body and a disruption in the flow will cause various health issues. The electromagnetic lines, also referred to as meridians, work in the body in a similar way as the electrical wiring in a house. When a circuit breaker "blows," a section of the house fed by that current line loses power. It has long been observed that the removal of "blockages" of the meridian lines will restore good health. Different means have been used to stimulate these lines such as sharp stones, bone needles, and eventually metal needles, as well as hand techniques. Other methods used to "open" the blockages in electromagnetic lines include taping stationary magnets to a patient, magnetic beds, foot pads, plasters, etc, as well as various other types of machines.

Muscle response testing is a diagnostic methodology that uses the principals of Applied Kinesiology for determining a body's needs. Muscle response testing (MRT) is used widely by medical doctors, acupuncturists, chiropractors, osteopaths, veterinarians, and holistic dentists. There have been a number of books written on MRT including a seminal work written by Dr. David R. Hawkins in 1995.

During MRT, medical personnel will push down on a patient's extended arm while the patient resists the downward pressure. If the patient's nervous system is irritated for a period of time, a temporary short circuit will arise in the nervous system causing the arm being tested to momentarily weaken. During testing, medical personnel will irritate the nervous system by touching a sensitive area of the body, an acupuncture point or even by generating uncomfortable or irritating thoughts. Medical personnel may also ask a series of "yes/no" questions of the nervous system, looking for a weak or a strong response of the patient's extended arm. The weak or strong response reveals information about troubled areas in the body and provides additional information to medical personnel on how to treat the troubled areas.

MRT is used for virtually any question that can be asked of the body to make determinations about physiology, skeletal trauma, allergies, nutritional imbalances, emotional states or anything that may affect the body or the mind. MRT is a diagnostic tool that is only limited to the creativity of the practitioner's ability to ask a proper question. Once the information is ascertained, muscle testing may then be used to find out what the body or mind will respond to in terms of a resolution to the problem. Another benefit of MRT is that many of the problems that may be detected using MRT cannot be detected using conventional lab and exam tests and thus, are not discoverable except when using MRT.

There have been many efforts directed to using muscle response testing and applied kinesiology techniques. For example, U.S. Pat. No. 5,188,107 discloses a bi-digital O-ring test for imaging and diagnosis of internal organs of a patient. During the test, a patient forms an O-ring with a first hand by placing the finger tips of his thumb and one of his remaining fingers together, and a sample of tissue of an internal organ is placed in contact with the patient's second hand. The patient's internal organ is non-invasively externally probed with a probing instrument. The internal organ is the same type of organ as that of the sample. Simultaneously, a tester attempts to pull apart the O-ring shape of the first hand by means of the tester placing his thumb and one of the remaining fingers of each of his hands within the O-ring shape of the patient to form interlocking O-rings and pulling the thumb and the finger of the patient apart due to an electromagnetic field of the tissue of the sample interacting with an electromagnetic field of the internal organ being probed. This interaction is detected by the ability to pull apart O-ring shape, thereby permitting imaging of the boundaries of the internal organ being probed.

U.S. Pat. No. 5,855,539 discloses a kinesiology testing apparatus having a base, and a foot treadle having a first end and a second end. The first end of the foot treadle is pivotally attached to the base. The apparatus includes a line having a first end and a second end, whereby the second end of the line is secured adjacent to the second end of the foot treadle. Means is provided for securing the first end of the line to a person's arm. When a person has his arm extended out parallel to a floor, a downward force exerted by a foot of the person upon the foot treadle transmits, via the line, a downward force upon the persons arm.

In spite of the above advances, there remains a need for improved systems, devices and methods for efficiently diagnosing medical conditions using muscle response testing and treating the medical conditions using magnetic devices.

SUMMARY OF THE INVENTION

In one embodiment, the present invention discloses a method and system for placing one or more magnetic devices, such as an octapolar magnetic device, at a location on the body that is determined through using muscle response testing (MRT). The placement of the one or more magnetic devices preferably stimulates the electromagnetic lines in the body causing the bioelectrical energy in the body to flow freely. When the rivers of bioelectrical energy flow freely (as taught by traditional Chinese, Japanese, Indian, and Korean medicine), the individual feels better and heals faster.

In one embodiment, the present invention relates to systems, device, and methods for the treatment of health issues related to the blockage of the electromagnetic lines of the body. A blockage may result from either a lack of sufficient bioelectrical energy flow, or because of too much flow in one line and not enough in another. It has long been known that when these electromagnetic lines in the body are hindered in some way it causes disease. By stimulating the bioelectrical flow (Chi in Traditional Chinese Medicine (TMC) and Ki in Japanese Medicine), a physical healing of a variety of issues may take place.

In one embodiment of the present invention, multi-polar magnetic devices are placed on one or more points or locations on the body that have long been used for the stimulation of bioelectrical energy flow that is crucial to good health. In one embodiment, a multi-polar magnetic device has two positive and two negative poles alternating diagonally at the corners within a square 2×2 grid within the same plane. A flux field produced by the magnetic device opens magnetic lines at the desired point for healing the patient.

In one embodiment, the magnetic device has four disc-shaped magnetic bodies that are housed in a non-metallic enclosure that holds the magnetic bodies in place and in relative alignment with one another. It is believed that the relative orientation of the magnetic discs relative to one another enhances the performance of the device, because their collective orientations combine to produce a suitable field gradient that properly stimulates the electromagnetic lines of the body. The magnetic device includes an enclosure that has a prominent directional arrow, which is an important element contributing to the effectiveness of the systems and methods disclosed herein because it enables medical personnel to properly orient the magnetic devices for maximizing therapeutic benefit.

More than one device may be worn at a time. The two or more devices are preferably used at different points or locations on the body, whereby the points or locations are determined through Muscle Response Testing (MRT). The multipolar magnetic devices are preferably not used in close proximity to one another, as doing so has been found to disrupt the field gradient of each apparatus.

The particular locations on the body used for the placement of the magnetic devices have been used for centuries in Eastern medicine. The placement of the magnetic devices at acupuncture points on the body is customized to a patient's needs. Through the relatively new science of Muscle Response Testing (MRT) or Manual Applied Kinesiology, blockages or points of correction on the body are located. After the exact placement points are identified, MRT is used again to determine one or more of the following: 1) the order of placement or placements, 2) the duration that each magnetic device will be left in place, 3) determining whether two or more device should be placed on the body at the same time or whether they should be placed one at a time in a series, and 4) determining whether the same placement series will be repeated or a new placement series will be used.

These and other preferred embodiments of the present invention will be described in more detail below.

BRIEF DESCRIPTION OF THE DRAWING

FIG. 3 shows a schematic top plan view of a multi-polar magnetic device, in accordance with one embodiment of the present invention.

FIGS. 4 and 5 show cross-sectional views of the multi-polar magnetic device of FIG. 3.

FIG. 7 shows acupuncture points and the main meridian channels on a human body.

FIGS. 8A-8D show Jin Shin Jyutsu points on a human body.

DETAILED DESCRIPTION

Figure 1:
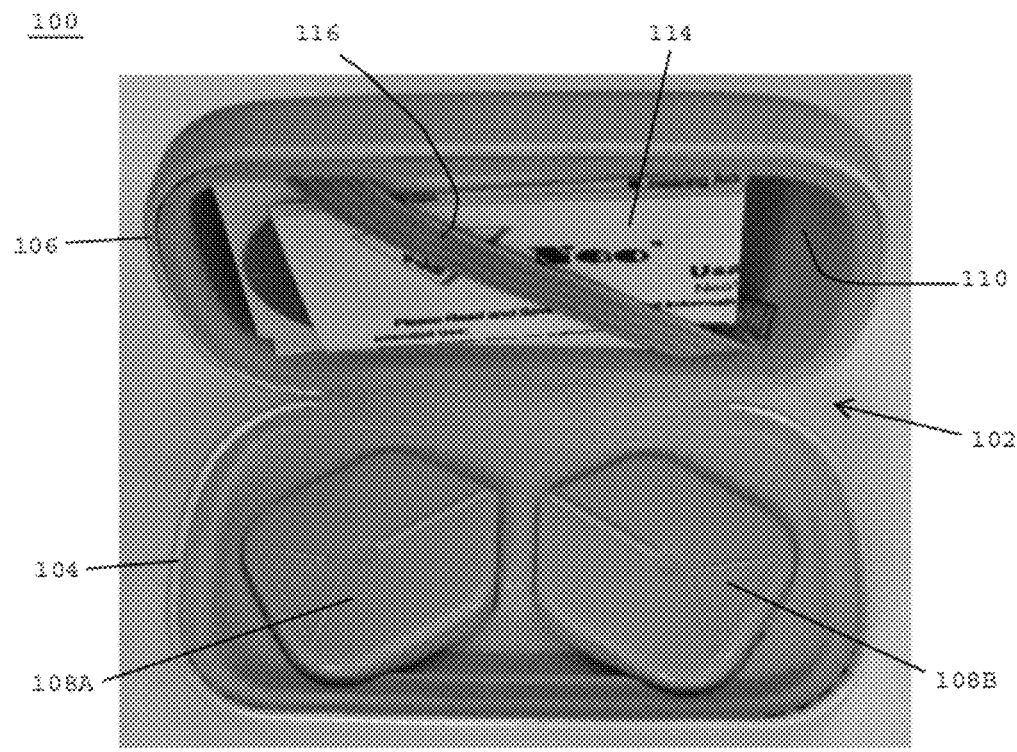
FIG. 1 shows a system for treating a patient including a pair of multi-polar magnetic devices, in accordance with one embodiment of the present invention.

Referring to FIG. 1, in one embodiment, a system 100 for treating medical conditions preferably includes a storage case 102 having a base 104 and a cover 106 that is hingedly connected with the base. The base 104 is adapted to receive and hold a pair of octapolar magnetic devices 108A, 108B, which may be removed from the base 104 for being applied to a patient. The cover 106 preferably includes an underside 110 adapted to receive a plurality of adhesive discs 112 for adhering the magnetic devices to a patient and an instruction manual 114 that provides instructions for using the octapolar magnetic devices 108A, 108B. An elastic band 116 is preferably secured to the underside 110 of the cover 106 for storing the adhesive discs 112, and the instruction manual 114 within the cover 106 of the case 102.

Figure 2A:
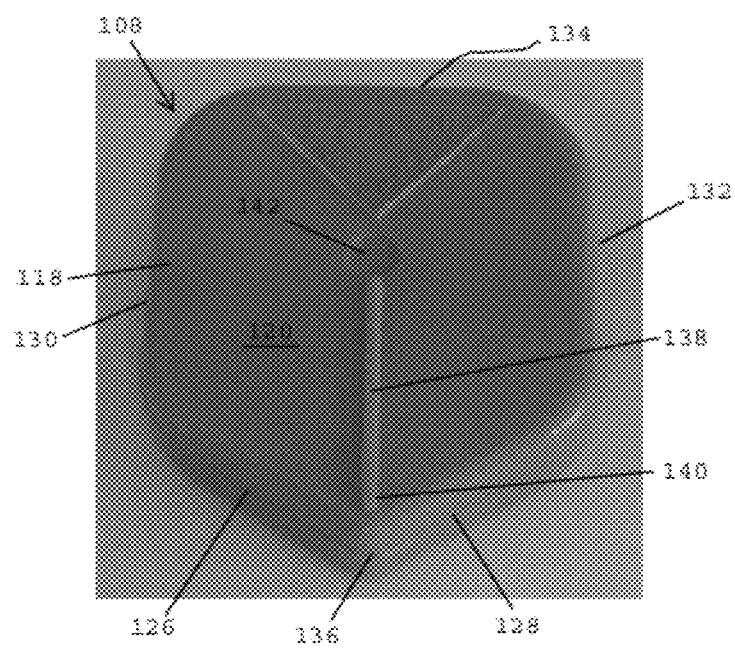
FIGS. 2A-2C show a multi-polar magnetic device, in accordance with one embodiment of the present invention.
Figure 2B:
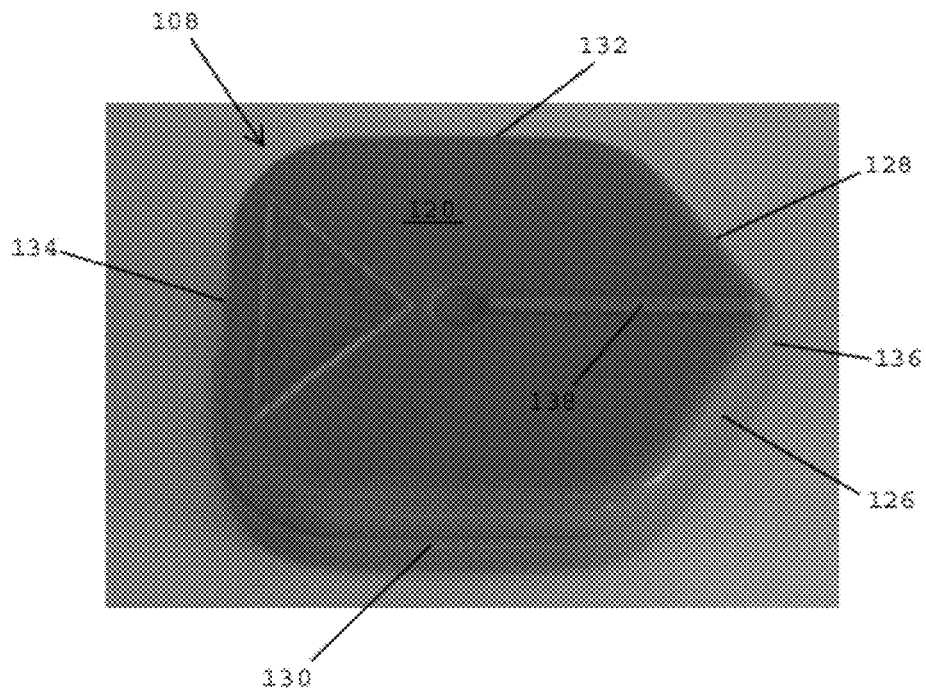
Figure 2C:
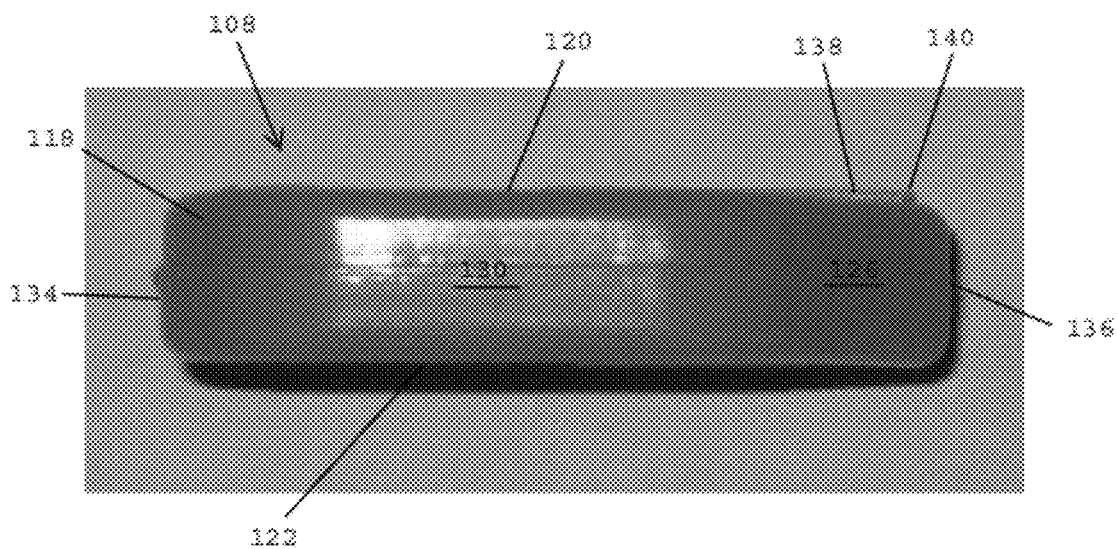

Referring to FIGS. 2A-2C, in one embodiment, an octapolar magnetic device 108 desirably includes a housing 118 made of a non-metallic material, such as a plastic or polymer material, that is adapted to house a plurality of permanent magnets therein. In one embodiment, the housing 118 has a top surface 120, a bottom surface 122, and a side wall 124 extending between the top and bottom surfaces. The side wall 124 preferably defines a pentagon shape and desirably includes a first side wall section 126, a second side wall section 128, a third side wall section 130, a fourth side wall section 132, and a fifth side wall section 134. The first and second side wall sections 126, 128 preferably join one another at an acute angle that defines an apex 136. The housing 118 also preferably includes an alignment marker 138 that is formed in the top surface 120 of the housing. A leading edge 140 of the alignment marker 138 is preferably aligned with the apex 136 of the housing 118. The top surface 120 of the housing 118 also preferably includes a central marker 142 that is desirably centered between the four magnetic discs located within the housing. As will be described in more detail herein, the alignment marker 138 enables the octapolar magnetic device 108 to be properly aligned on a patient's body for maximizing therapeutic benefit.

Referring to FIGS. 3-5, in one embodiment, the octapolar magnetic device 108 desirable includes four magnetic discs 144, 146, 148, and 150 that are held by the housing 118 in a particular orientation that accounts for the magnetic properties of each magnetic disc, and so that the magnetic device 108 may be easily handled without altering the arrangement of the magnetic discs. In one embodiment, each of the magnetic discs is preferably a cylindrical, center-charged permanent magnet with each magnetic disc being of equal size and strength. The magnetic poles of the magnetic discs are desirably disposed substantially in two parallel planes, with each plane containing opposing positive and negative magnetic poles. Referring to FIG. 3, in one embodiment, first and third magnetic discs 144, 148 have their negative charged faces in a first plane and second and fourth magnetic discs 146, 150 have their positively charged faces in the first plane. Collectively, the four magnetic discs form an octapolar magnetic device.

In one embodiment, a first face 152 of the first magnetic disc 144 lies in a first plane P1 and is negatively charged and a second face 154 of the first magnetic disc 144 lies in a second plane P2 and is positively charged. Thus, a negative magnetic pole of the first magnetic disc 144 is centered on the first plane P1, while a positive magnetic pole of the first magnetic disc 144 is centered on the second plane P2. The housing 118 holds the second magnetic disc 146 adjacent the first magnetic disc 144. A first face 156 of the second magnetic disc 146 lies in the first plane P1 and is positive charged and a second face 158 of the second magnetic disc 146 lies in the second plane P2 and is positively charged. Thus, a positive magnetic pole of the second magnetic disc 146 is centered on the first plane P1, while a negative magnetic pole of the second magnetic disc 146 is centered on the second plane P2.

The four magnetic discs 144, 146, 148, 150 are desirably oriented to define four vertices of a quadrilateral shape. The four magnetic poles in each of the two parallel planes comprise two positive and two negative poles, the two positive poles defining two diagonal vertices and the two negative poles defining the diagonal vertices of the quadrilateral shape. The distance between the poles in each plane is such that the magnetic field generated by each pole has a significant magnitude at each of the other poles Referring to FIG. 3, the negatively charged faces of magnetic discs 144 and 148 and the positively charged faces of magnetic discs 146, 150 are in the first plane P1 (FIG. 4). The two negative poles on discs 144, 148 define opposite diagonal vertices of the quadrilateral shape, while the two positive poles on discs 146, 150 define opposite diagonal vertices. Each of the four magnetic poles is magnetically attracted by the two oppositely charged poles and is magnetically repelled by the like charged pole Referring to FIGS. 3 and 5, the magnetic discs preferably have the same diameter, height and shape. In one embodiment, each magnetic disc has a diameter of about 12.7 mm and a height of about 3.2 mm. However, larger or smaller magnetic discs may be used and still fall within the scope of the present invention. When cylindrical magnetic discs with opposite poles on opposite faces are utilized, both major faces of the octapolar magnetic device 108 will exhibit the same magnetic field. Thus, each major face of the octapolar magnetic device can be considered to have a quadrapolar configuration In one embodiment, each of the magnetic discs preferably center-charged, which means the magnetic energy is concentrated on the central axis of each magnetic disc rather than being distributed uniformly over the face of the magnet. The magnetic induction field over the center-charged face has a steeper gradient than the field over a non-center-charged face. Suitable center-charged magnets are manufactured by Delco Remy, a division of General Motors Corporation.

The housing 118 preferably holds the magnetic discs 144, 146, 148 and 150 in the desired orientation. The housing 118 may be made of a thermoplastic material in which the four magnetic discs are held.

The alignment marker on the magnetic device has great importance regarding the treatment methods disclosed herein because the energy flow in bodies can become disrupted, thereby causing a variety of health issues. Energy can become stagnated, thus needing to be dispersed or it can be lacking in an area and need more from other areas to bring it into balance. In Jin Shin Jyutsu and other similar techniques, this is done by directional hand placement. The energy flow of the body is influenced by the way the hands are placed while the patient is being worked on by the practitioner. In the present invention, it is done by the use of the alignment marker and how the magnetic devices are oriented on the body. This is very important in achieving the re-establishment of proper energy for resulting in the elimination of disease. The alignment marker on the magnetic device influences the path and the direction of the energy flow in the body in the same way.

Figure 6A:
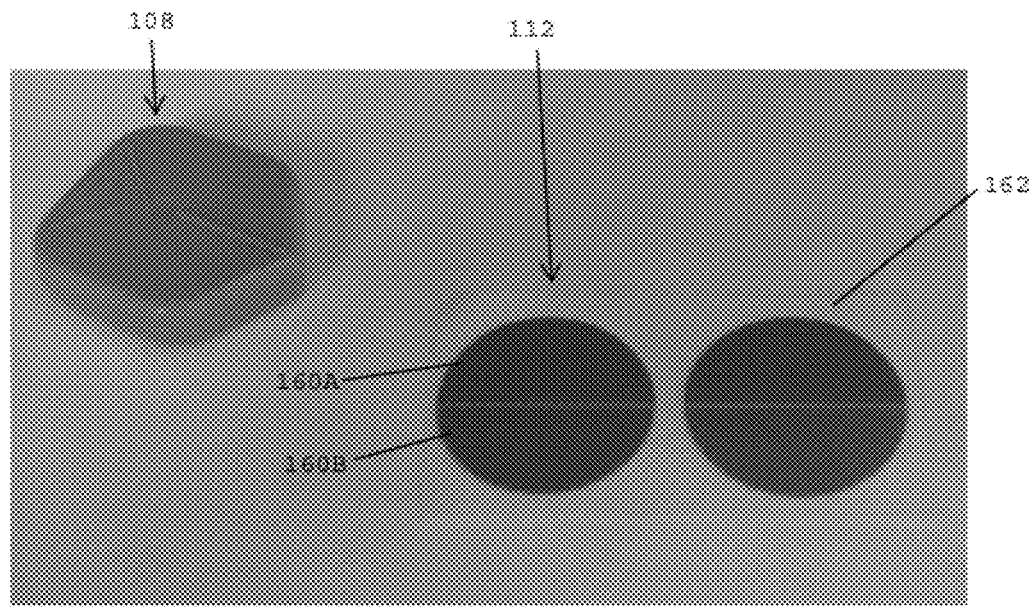
FIGS. 6A-6F show a method of attaching a multi-polar magnetic device to a patient, in accordance with one embodiment of the present invention.
Figure 6B:
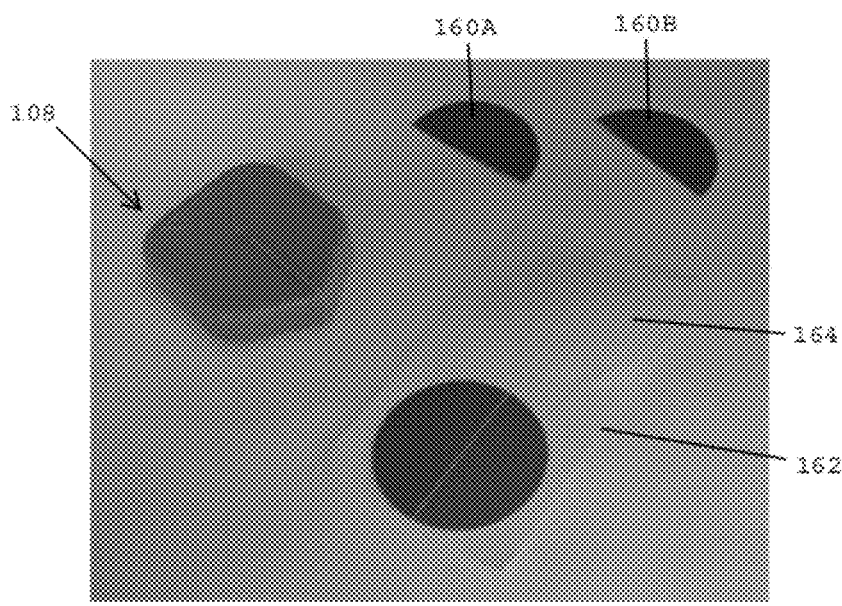
Figure 6C:
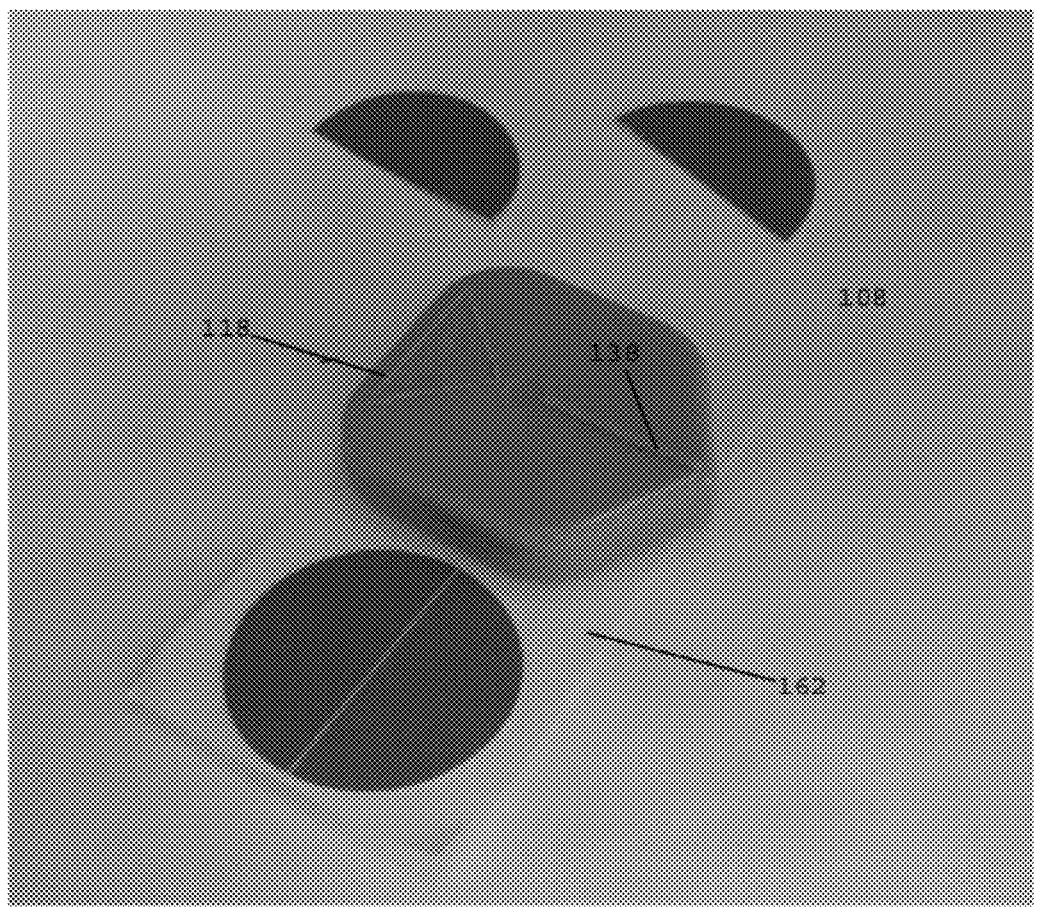

Referring to FIGS. 1 and 6A-6F, in one embodiment, at least one of the octapolar magnetic devices 108 is attached to a patient's body. Referring to FIGS. 1 and 6A, one of the magnetic devices 108 and at least one adhesive disc 112 is removed from the case 102. Referring to FIGS. 6A and 6B, a pair of tabs 160A, 160B is peeled away from a sheet 162 to expose a top face of an adhesive disc 164, which is preferably transparent. Referring to FIG. 6C, the bottom major face 122 (FIG. 2C) of the housing 118 is preferably pressed against the exposed adhesive disc 164 on the sheet 162 to secure the adhesive disc to the housing 118. The adhesive disc 164 is preferably attached to the bottom major face of the housing 118 so that the alignment marker 138 on the top major face 120 may be used for aligning the magnetic device on a patient.

Figure 6D:
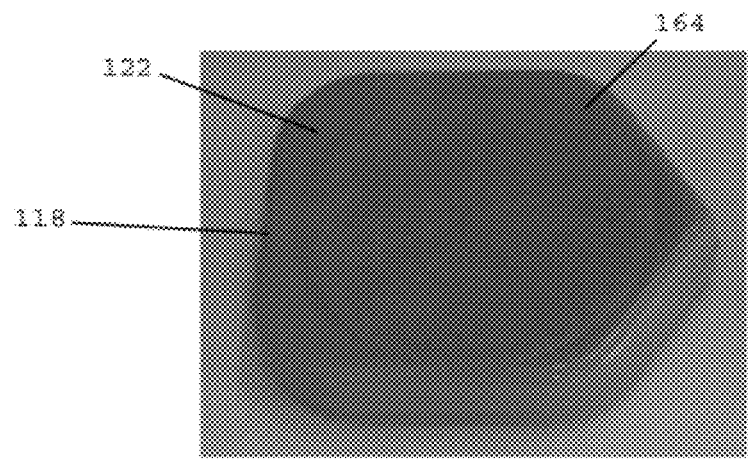
Figure 6E:
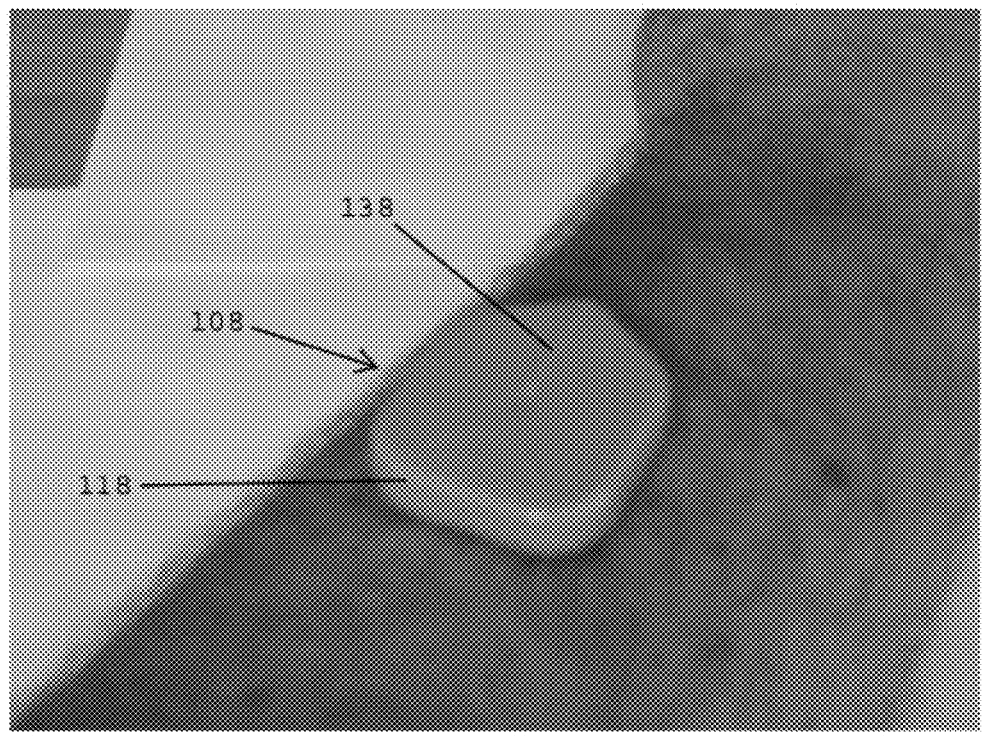
Figure 6F:
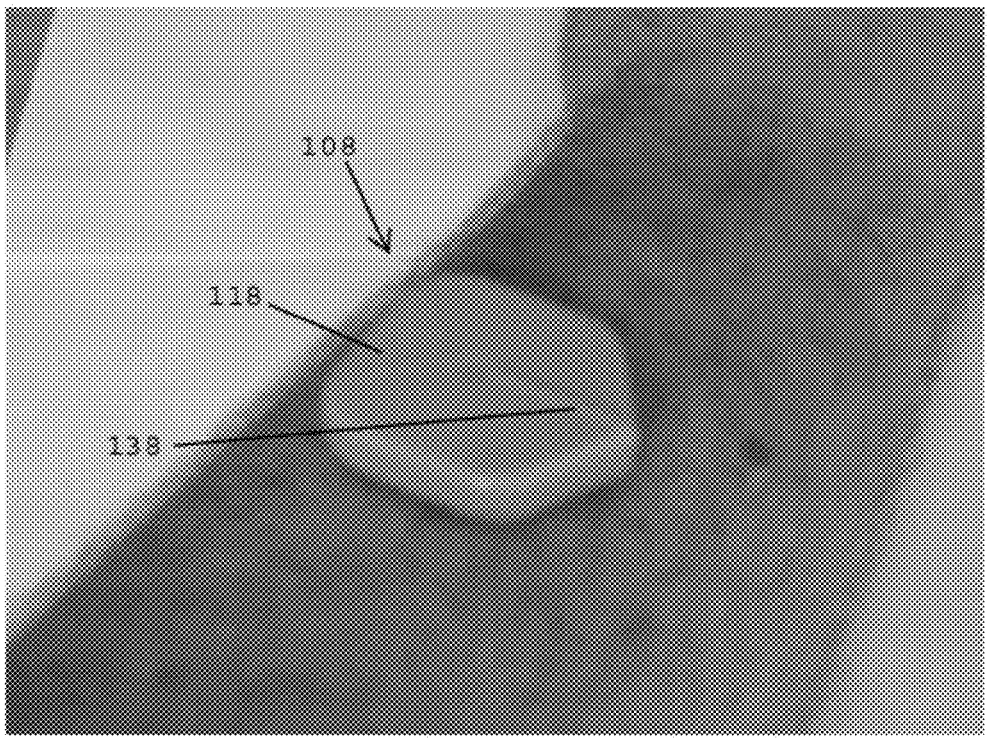
Figure 8C:
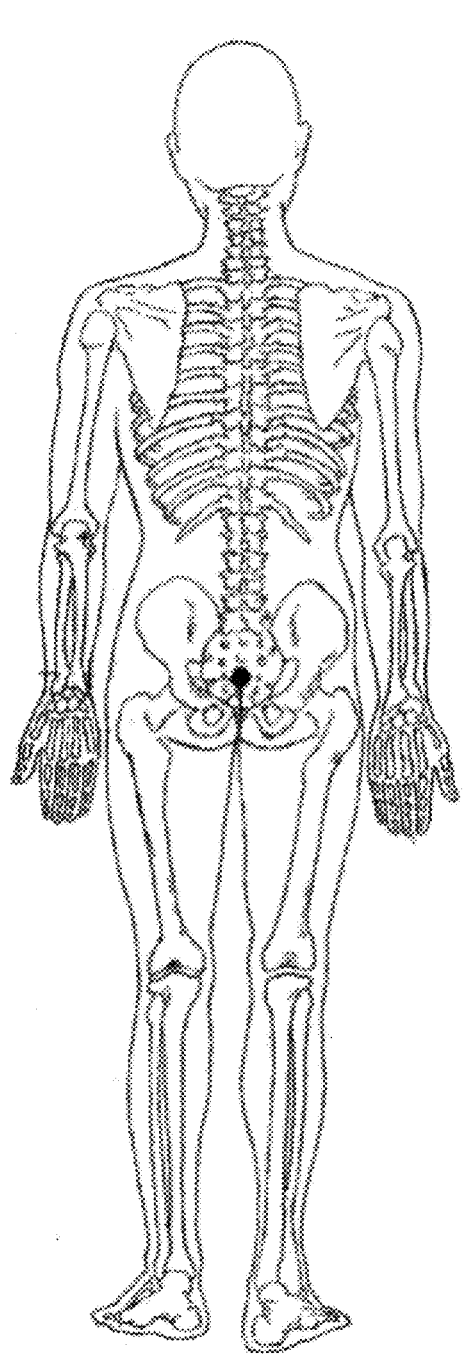
Figure 8D:
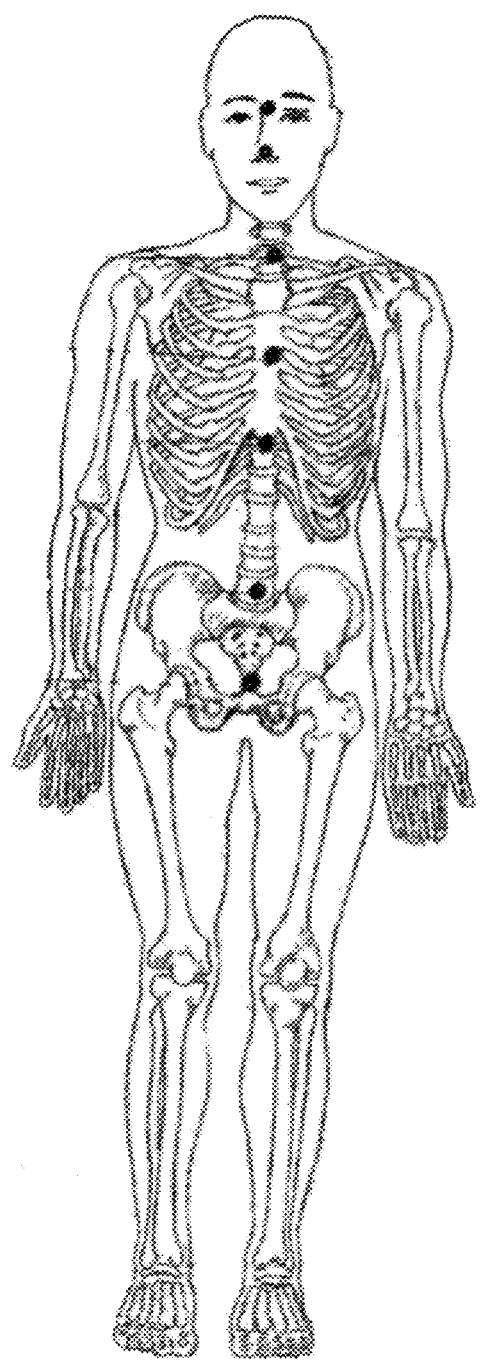

FIG. 6D shows the adhesive disc 164 after it has been attached to the bottom major face 122 of the housing 118. Referring to FIG. 6E, the housing 118 is preferably secured to a patient's body by pressing the adhesive disc 164 (FIG. 6D) and the bottom major face 122 of the housing 118 against the patient's skin. The alignment marker 138 on the housing 118 is used for properly aligning the magnetic device 108 on the patient for maximizing therapeutic benefit. In FIG. 6E, the alignment marker 138 and the magnetic device 108 are aligned at a six o'clock position. In FIG. 6F, the alignment mark 138 and the magnetic device 108 are aligned at a nine o'clock position. The orientation of the alignment marker is determined through muscle response testing as will be described in more detail herein.

Figure 9:
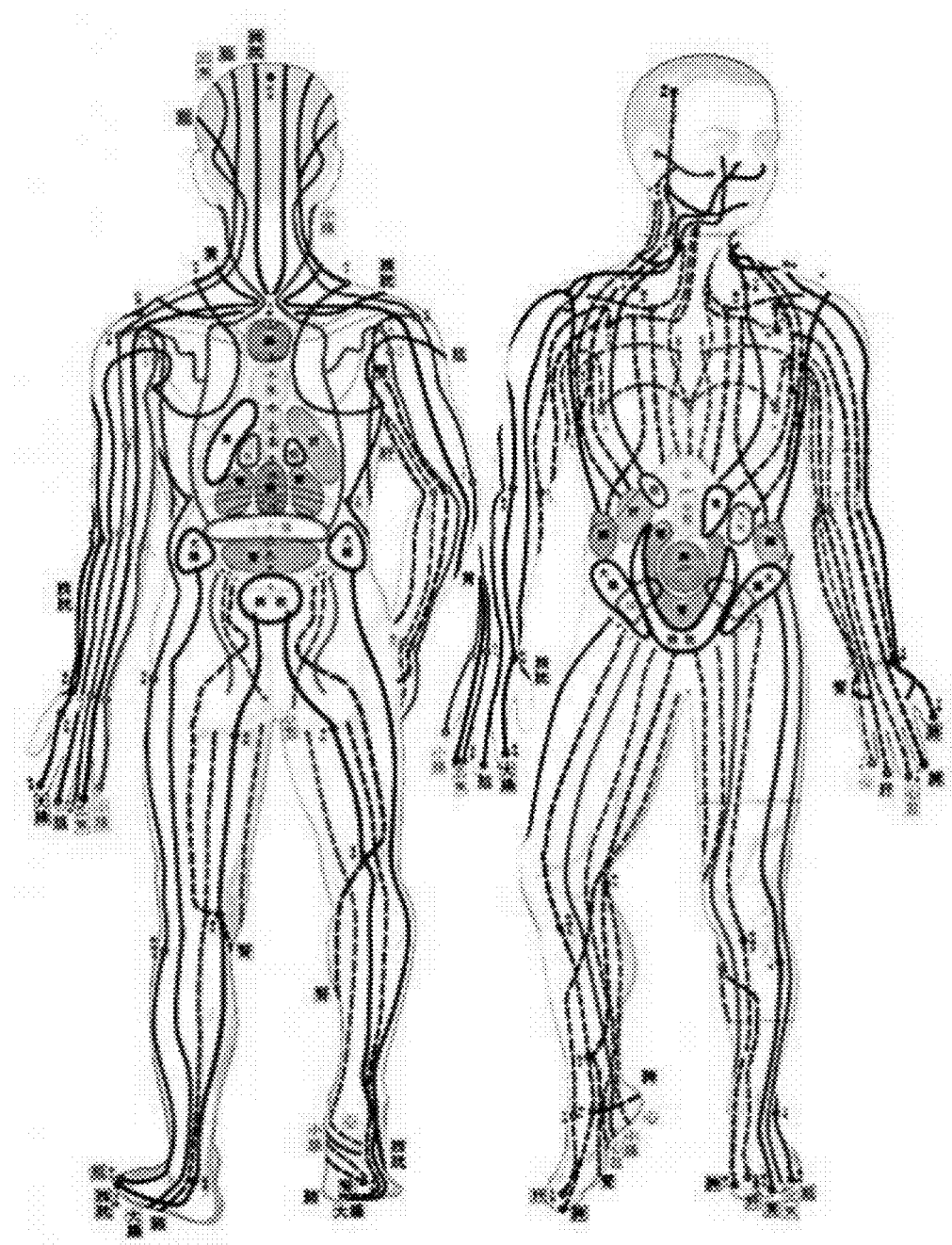
FIG. 9 shows meridian lines in a human body.

In one embodiment, one or more magnetic devices are placed at locations or points on the body that are widely used in acupuncture, acupressure, Shiatsu, Jin Shin Jyutsu, and reflexology. The locations may also be acupuncture points, electromagnetic lines, meridians, points used in traditional Chinese medicine, locations on the body used in Jin Shin Jyutsu, and locations on the body used in Ki-Iki Jutsu® and Shiatsu. FIG. 7 shows the location of traditional acupuncture points and the main meridian lines on a human body. FIGS. 8A-8D show the location of Jin Shin Jyutsu points on a human body. These points have been observed to have more electrical current than surrounding areas of the body so that they may be used to stimulate the electromagnetic lines or flows of the body. FIG. 9 shows the electromagnetic lines that extend through a human body.

There is a very strong connection between the brain and the muscles of the body. The brain uses electrical current to direct muscular movement. This relationship makes the muscles very sensitive to the electrical flows of the body, thus making them good indicators of the strengths and weaknesses of the meridian lines or flows.

In one embodiment, a patient is assessed using Muscle Response Testing (MRT) or Manual Applied Kinesiology (AK). MRT is an effective way of determining energy pathways that are disrupted.

In one embodiment, one muscle is isolated, usually the deltoid, and consistent pressure is put upon it by gently but firmly pressing downward on the arm. Other muscles may be tested, however, the deltoid muscle is most commonly used for testing. When meridian line or flow weakness or blockage is identified through the electrical response of the muscle, the same technique may be used to determine which therapies are needed to strengthen the line and restore flow once again. The process is somewhat similar to finding a "blown" fuse in an electrical system in a house and replacing it to restore the electrical circuit and its flow of current.

When a patient/client is about to be tested, the first step is to check the polarity of the individual. As used herein, the terms patient and client may be used interchangeably. The Earth is a huge magnet and the body acts as an electromagnetic. There is a magnetic difference between the top of a patient's head (North Pole), and the bottoms of the patient's feet (South Pole). There is also a difference in the patient's hands, with the palm of the hand being the South Pole and the back of the hand being the North Pole.

Figure 10A:
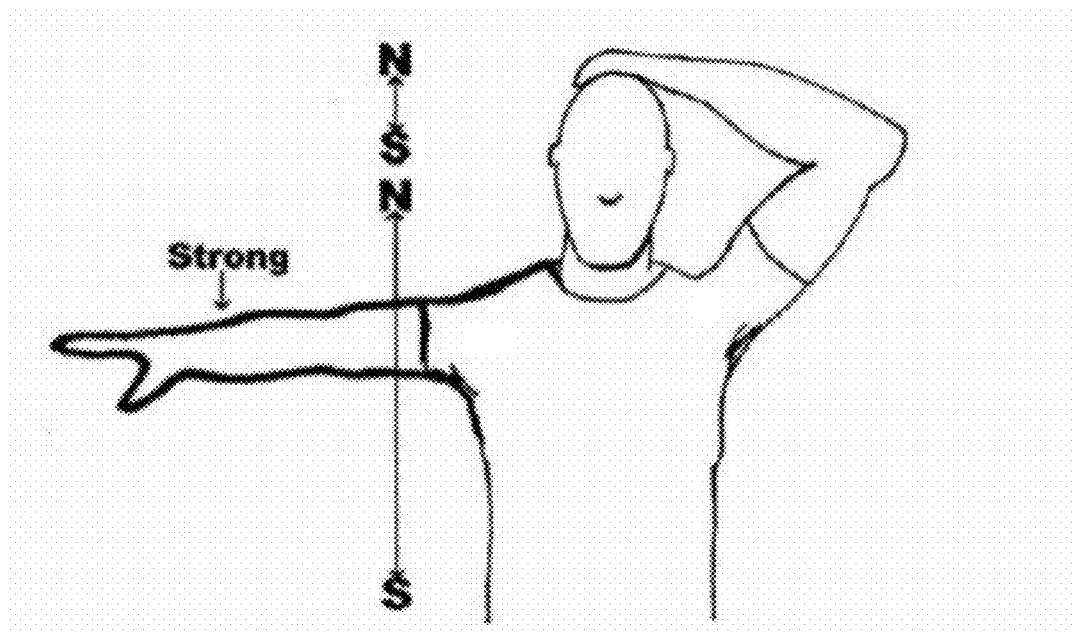
FIGS. 10A and 10B show a method of testing a patient, in accordance with one embodiment of the present invention.
Figure 10B:
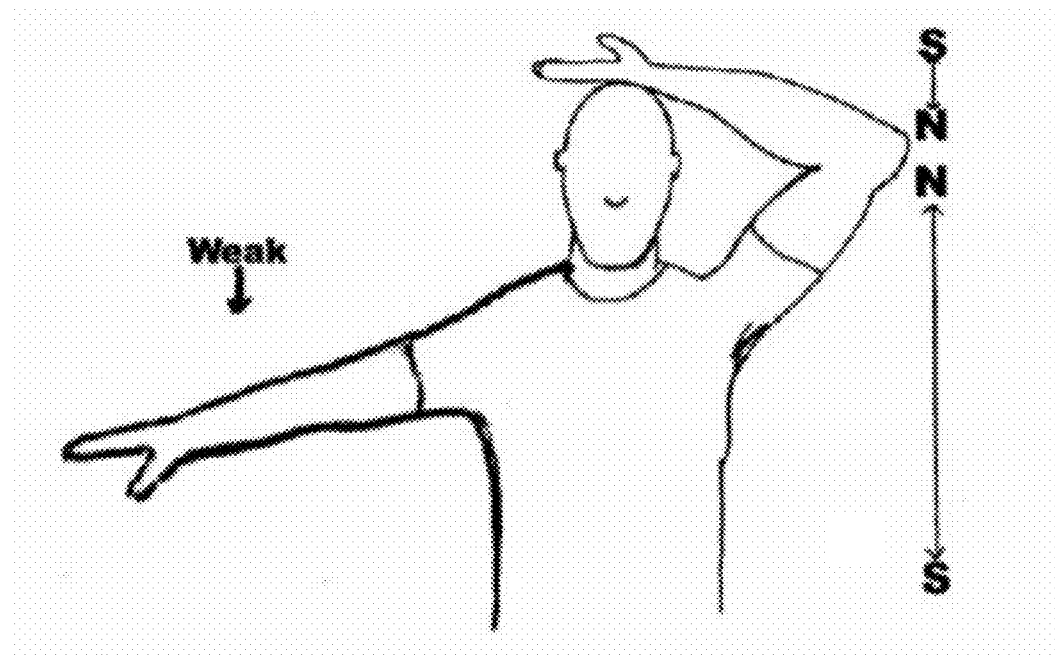

Normal Polarity. Referring to FIGS. 10A and 10B, when the back of the hand is placed on the top of the patient's head, if the individual's polarity is correct, the deltoid (or whatever muscle is being used) will register weakness, and the arm will weaken. The reason for this is that the patient has two like magnetic poles. The top of the head is North, and the back of the hand is North, and as with any other type of magnet two similar poles will repel each other. The patient cannot feel the repulsion but the brain and the nervous system perceive it immediately and the inner reflexes to all the muscles are slightly weakened.

Normal Polarity. When the patient places the palm of the hand on the top of the head, if the individual's polarity is correct, the deltoid (or whatever muscle is being used) will register strength. The reason for this is that the patient has two opposite poles. The top of the head is North and the palm of the hand is South so there is an attraction, whereupon the computer in the brain is not affected so that the muscles keep their strength.

Unstable Polarity. Unstable polarity exists when the palm of the hand is placed on the top of the head and there is no change in the strength of the muscles. If the patient places the palm of the hand on the top of the head and the muscles weaken, this is an indication of a problem that must be corrected before the test can begin. The usual causes of polarity issues in the body are lack of water, structural ankle issues, heavy jewelry (metal will disrupt electrical flow), and occasionally cell phones. When the above polarity disturbances occur, which is not common, they must be corrected before continuing.

Figure 11A:
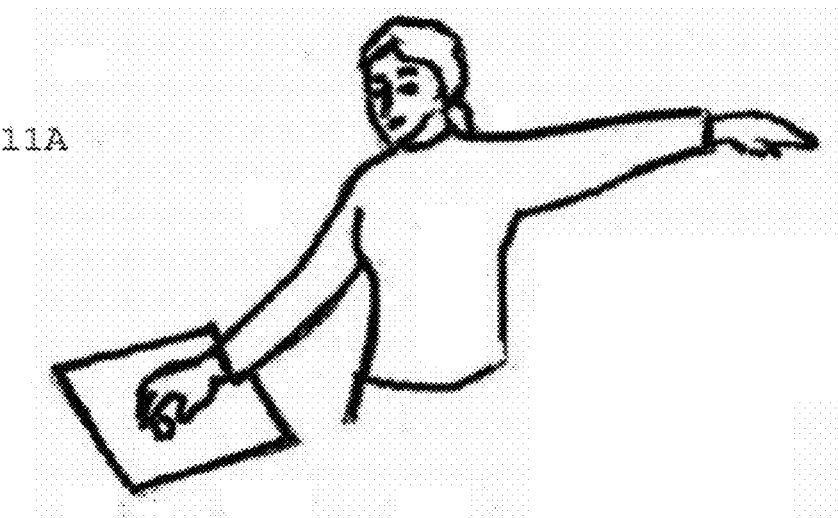
FIGS. 11A-11C show a method of testing a patient, in accordance with one embodiment of the present invention.
Figure 11B:
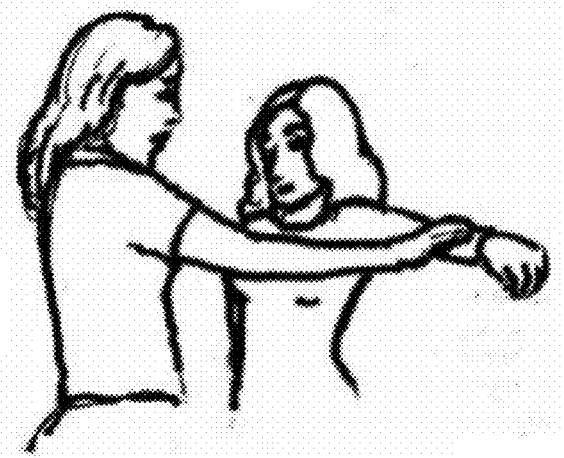
Figure 11C:
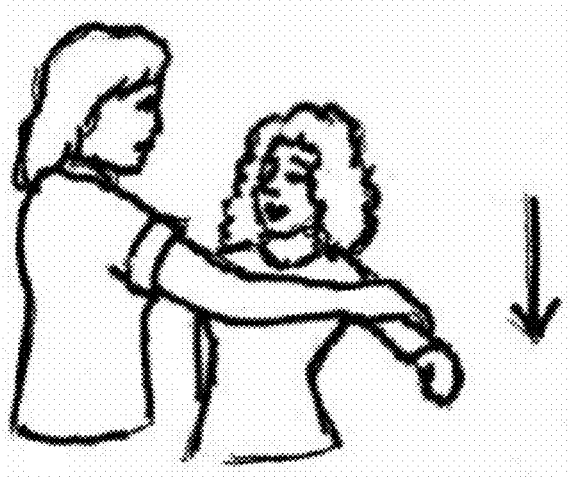

In one embodiment, Muscle Response Testing (MRT) is used to determine if the system and methods will work for the patient. Referring to FIGS. 11A-11C, in one embodiment, the patient can hold a magnetic device in their hand and the muscles will respond with either strength or weakness. If the arm tests strong while holding the device, that indicates that the magnetic therapy will work well for the body in promoting healing. If the muscle displays weakness while the individual holds the device that indicates that the therapy would not be the optimum method to promote healing. If the patient touches the magnetic device and the muscle displays strength that indicates that the system and methods will work well and help promote healing. The patient can also touch a device and if their arm is weak it would not be the best method to promote healing in their case.

After getting a positive response that the magnetic devices will benefit the patient, a determination is made regarding where the device is to be placed on the patient's body. This is once again determined by MRT. The locations or points chosen are ones used for centuries to stimulate the electromagnetic lines or flows in the body. The patient's symptoms help guide the practitioner to the proper location but finding the exact spot of placement is a process of elimination. Referring to FIG. 8B, in one embodiment, point #4 located at the base of the skull on the right side of the body is used. When the #4 location is pointed to and the deltoid responds with strength the tester knows there is not problem along this energy flow or line. If the #4 location is pointed to and the response is a weakening of the deltoid muscle the indication is there are issues with this line or flow in the body and a device should be placed there. This process is used to check the points or locations of the body that could be used for possible device placement. The confirmation of the #4 location is in agreement with the patient's symptoms because they suffer with headaches that occur mostly in the area of the forehead, they get neck pain, and have a very stubborn personality, all of which originate with a malfunctioning of the #4 flow.

Figure 12A:
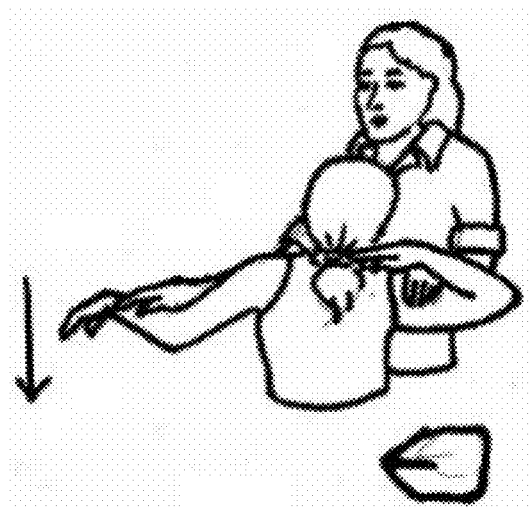
FIGS. 12A-12C show a method of testing a patient, in accordance with one embodiment of the present invention.
Figure 12B:
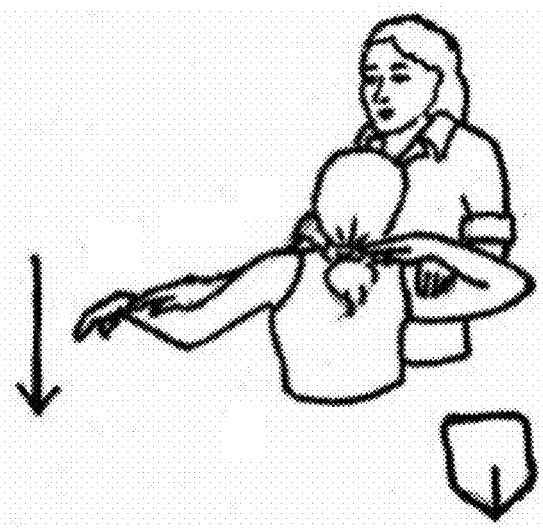
Figure 12C:
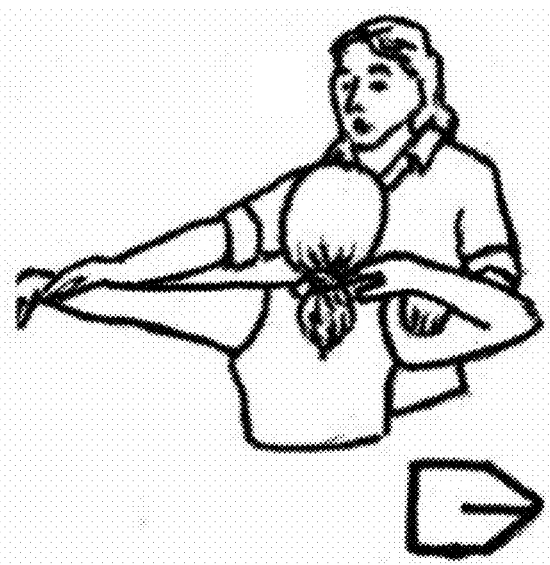

Next, MRT is conducted for determining the direction of the arrow on the magnetic device when the device is placed on the patient's body. The direction of the arrow will directly impact the success of the treatment methodology because the electromagnetic lines or flows run in many different directions. The tester uses a process of elimination. Testing is conducted with the arrow on the magnetic device pointed in each direction, one at a time, by either placing the device on the patient or letting the patient hold the device and shift the arrow each time a test is conducted. Referring to FIG. 12A, in one embodiment, the alignment marker 138 on the magnetic device 108 is pointed to the individuals left, the deltoid goes weak, which is a negative response, and the body's answer is "no." Referring to FIG. 12B, in one embodiment, the alignment marker 138 on the magnetic device 108 is pointed down, the deltoid goes weak, which is a negative response, and the body's answer is "no." Referring to FIG. 12C, in one embodiment, the alignment marker 138 of the magnetic device 108 is pointed to the patient's right, the deltoid muscle is strong, and the body's answer is "yes." Based upon the above scenario, the magnetic device is placed on the #4 point, on the right side of the body, with the directional arrow pointing to the patient's right.

If none of the tested arrow directions (i.e., up, down, left or right) provided a "yes" response, then the MRT testing will be conducted using the face of a clock. In one embodiment, the directional arrow is placed between 1 and 3 o'clock. The deltoid muscle is weak so the patient's body does not want the arrow in this direction. Next, the placement arrow is positioned between 3 and 6 o'clock, the deltoid is weak, a negative response, the body does not want the arrow in this direction. Next, the directional arrow is positioned between 6 and 9 o'clock, the deltoid muscle is strong indicating a positive or a yes, which means that the body wants the directional arrow pointing between 6 and 9 o'clock. Because it was already determined that the body did not test for the arrow direction to be down or to the right or left, there is no need to test for the 6 o'clock or 9 o'clock directions. The next test is the 7 o'clock direction, the deltoid goes weak, a negative response, the body does not want the 7 o'clock direction. The directional arrow is then placed in the 8 o'clock direction and the deltoid muscle is strong indicating a positive response, the body wants the arrow pointed in this direction. The testing indicates that the magnetic device should be placed on the right #4 location with the directional arrow pointing to 8 o'clock.

In one embodiment, a determination is made regarding how long the magnetic device should be worn on the body. Again, this determination is preferably made through a process of elimination using MRT. In one embodiment, time is grouped in blocks to facilitate the test. For example, the device will be worn for 10 hours, the deltoid goes weak, a negative response, it will not be worn for 10 hours. The device will be worn under 10 hours, the deltoid is weak, a negative response, the device will not be worn under 10 hours. The device will be worn over 10 hours, the deltoid is strong, a positive response. How much over 10 hours? The device will be worn for 15 hours, the deltoid is weak, and will not be worn for 15 hours. The device will stay on for under 15 hours, the deltoid is strong, indicating a positive response by the body. This result indicates that the device should be worn for between 11 and 14 hours. The test continues. The device will stay on the body for 11 hours, the deltoid is weak, a negative response. The device will be left on the body for 12 hours, the deltoid is weak, a negative response. The device will be left on for 13 hours, the deltoid is weak, a negative response. The device will be left on for 14 hours, the deltoid is strong, a positive response. The test results indicate that the device should be placed on the right #4 location with the arrow direction at 8 o'clock for 14 hours.

The next stage of testing is used to determine if the device placement will be re-applied. This can be determined by asking "will the placement need to be re-applied?" or having the patient hold the device by the #4 location. If the deltoid is weak, the answer is negative, a no. If testing indicates the deltoid is strong, the answer is positive, a yes.

During testing, statements are verbalized initiating a response from the brain that affects the deltoid (or whatever muscle is chosen for testing). The device placement on the body will be re-applied two times, the deltoid is strong, a positive response, it will be repeated two times.

For determining whether the device should be reapplied in the location, duration, and direction, the following questions are asked. The device placement will be worn two days in a row, the deltoid is weak, a negative response, it will not be worn two days in a row. The statement is then made that the device placement on the body is spaced every other day, the deltoid is weak, a negative response, it will not be repeated every other day. Placement on the body will be repeated every third day, the deltoid is strong, a positive response, the device will be worn on the body for 14 hours, taken off, and repeated again for 14 hours 3 days later.

Based upon the above responses, the device needs to be worn on the right #4 location with the arrow toward 8 o'clock, for 14 hours. After the 14 hours is complete, the device is to be removed. On the third day after removal the device is to be reapplied to the body at the same location, with the arrow direction to be the same, and the amount of time left on the body to be the same.

MRT is conducted to determine if a second placement is needed to further improve line flow. The deltoid is weak, a negative, no. Another placement will not be needed. If the test had been positive, the above process would be repeated for determining the location, direction, and length of time for placement of the second device.

Multiple Device Placement. The number of placements on the body may vary. In one embodiment, a determination is made if the method will benefit the health of the patient. The patient touches the device on a table, the deltoid is strong, a positive response, the individual would benefit from the method. The patient holds one device in their hand and a statement is made that only one location will be needed. The deltoid goes weak, indicating a negative response. The patient holds two devices in their hands and a statement is made that two locations will be needed. The deltoid is strong, indicating a positive response, the body wants devices in two locations on the body.

Testing is now conducted to determine where the two separate locations are on the body. The average number of devices is usually between one and three but can go higher in some cases. Another way to test for locations is to have the patient touch one device on a table, if the deltoid is weak, it is a negative response and more than one device is needed.

The patient touches two devices on the table, the deltoid is strong, a positive response from the body. This indicates that there should be two locations on the body for placement of the devices.

The patient is tested to determine if the locations to be used are used in Jin Shin Jyutsu, the deltoid is strong, indicating a positive response, we are looking for locations used in Jin Shin Jyutsu.

To facilitate the test, the body is broken up into sections. The points are located below the waist on the front of the body. The deltoid is weak, a negative response, the locations are not on points below the waist on the front of the body. The points are located below the waist on the back of the body. The deltoid is weak, a negative response, the locations are not on points below the waist on the back of the body. The points are located above the waist, the deltoid muscle is strong, a positive response, either one or both will be located above the waist. Testing has indicated that the point or points are located above the waist. The next section tested is above the waist on the back of the body. The deltoid muscle is weak, a negative response, the location is not on the back of the body.

Through a process of elimination it is determined that at least one or both of the locations are on the front of the body. This is confirmed by further testing. The deltoid muscle is strong indicating the device or devices will be placed on locations on the front of the body above the waist.

To find the exact location, each point will be tested by either the patient or the practitioner pointing to the area. In this case a weakness on the spot is the signal by the brain via the deltoid muscle indicating a line flow problem. One location has been found on the front of the body, the energy lock or sphere #22 (FIG. 8A). When the left #22 location was touched either by the patient or the practitioner, the deltoid weakened indicating line flow disruption. The directional arrow is then tested as previously discussed and the arrow will be facing to the patients' right.

At this stage, only one of the two locations has been identified for the particular placement. The testing continues for the second location by testing the arms. The deltoid is strong when the right arm is tested, a positive, yes. The second area of placement is located on the right arm. Again by process of elimination the points on the right arm are each tested and the location that shows up as weakness in the deltoid, indicated by the arm becoming weak, is the #19 (FIG. 8A) by the bend of the elbow. Through a process of elimination, it has been determined that the second location is the energy lock or sphere #19 on the right arm. The directional arrow will then be tested as described previously. In this case the arrow direction will by facing down toward the fingers.

For the double device placement it has been determined that the areas of placement will be the left #22 and the right #19. Testing is then conducted to determine if both devices are placed on the body at the same time. The deltoid is weak, a negative response from the body. The devices will not be placed on the body at the same time.

Testing is conducted to determine if the #19 will be placed on first, the deltoid muscle is weak, a negative response, the #19 will not be placed on the body first. Testing is conducted to determine if the #22 will be placed on the body first, the deltoid is strong, a positive response from the body, the device will be placed on the #22 first with the arrow direction pointing to the patient's right. The amount of time it will be worn on the body alone is then tested as described previously. It is determined that the left #22 will be worn on the body first, with the arrow direction to the patient's right, and is worn alone on the body for 5 hours.

Testing is then conducted to determine what will occur after the 5 hours have passed. The #19 device is placed on the right arm. Both the #22 and the #19 devices are worn on the body together for a MRT time of 10 hours. Testing is conducted to determine what will occur after the 10 hours is complete. The #22 is to be removed and the #19 will stay on the arm another 5 hours alone on the body. After the 5 hours is complete all devices are removed. Testing is conducted to determine if the placements will be repeated when the 20 hours of initial placement is completed, or will another placement or placements be needed after the first round of placements. The deltoid muscle is strong, a positive response, another placement or placements will be needed.

In one embodiment, an individual may conduct MRT on himself, which enables the individual to quickly care for an injury or illness. Teaching MRT to a non-practitioner will enable individuals to care for common health issues such as virus, flu, injuries, etc. Deeper levels of line correction would require a qualified practitioner or trained medical professional.

Self test method #1. In one embodiment, the finger pad of the thumb and the finger pad of one of the fingers, usually the pointer or middle, are gently slid against each other. If the fingers are dry there should be very little to no resistance to this movement. If something is placed in the opposite hand that is good for the body, the individual will feel resistance between the two fingers and a feeling of tackiness will develop. If something is placed in the opposite hand that is not good for the body, then there will be no change or the slip of the fingers increases. This method can also be used to isolate locations on the body that show blockage. The regular protocol for MRT can be followed.

Self test method #2. This method uses a finger loop. The muscles of the fingers are used to evaluate the needs of the body. The fingers on one hand create a loop and, using the finger of the opposite hand, an individual gently applies pressure to try to break the looped fingers apart. If the individual cannot pull the finger through the loop that would be a strong or positive test. It is making the body's electrical flow stronger. If the individual is able to pull the finger through it is making the body's electrical flow weaker. This test uses the same principle that are used when MRT the arm. Once again the MRT protocol for the therapy is followed. Although two self tests are disclosed, there are other self test methods that may be used.

Other ways to access line or flow blockages. Taking a pulse reading, which is used extensively in TCM, can help determine which lines or flows are problematic. From this information, the practitioner or medical professional can press on the locations that correlate to the lines having difficulty. The areas where devices should be placed will most likely be tender, and sometimes even painful. They can also feel like small hard nodules or lumps, and at times can feel as though there is a little electrical buzz or a pulse. It would then be up to the discretion of the practitioner as to how many devices would be needed, the duration, and the direction of the arrows.

Any method of identifying meridian or line flow blockage can be adapted to the methods disclosed herein in the same manner as described herein. Methods to access line or flow issues range from machines that use points on the feet and hands, using points on the body, TCM face reading techniques, nail reading, iridology (reading the eye), and sclarolegy (reading the whites of the eyes).

Figure 13A:
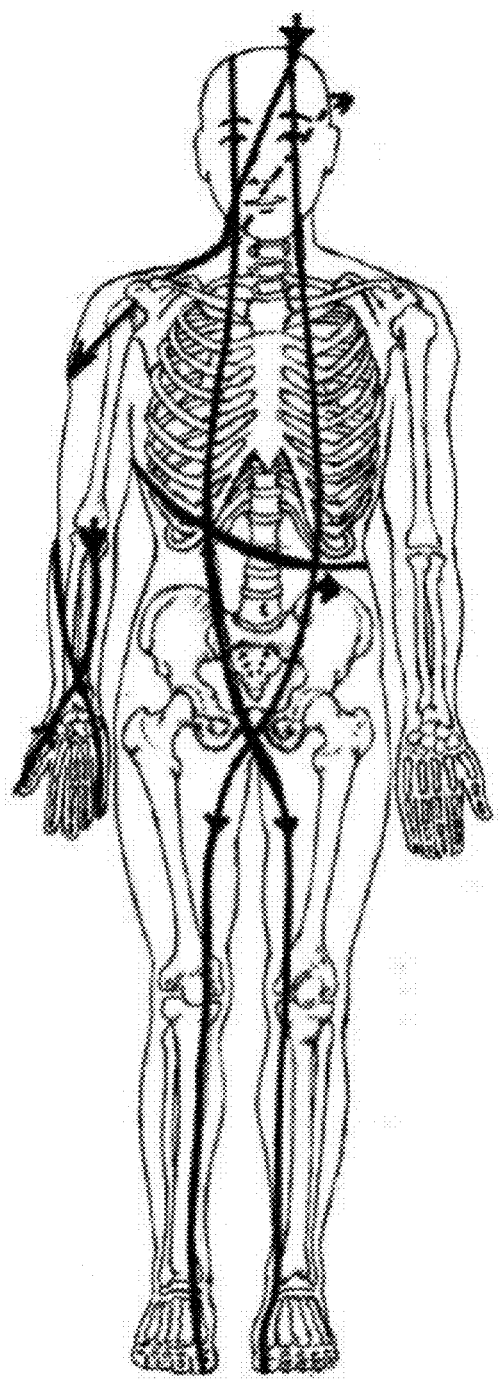
FIGS. 13A-13B and 14 show some examples of the direction of energy flow through a human body.
Figure 13B:
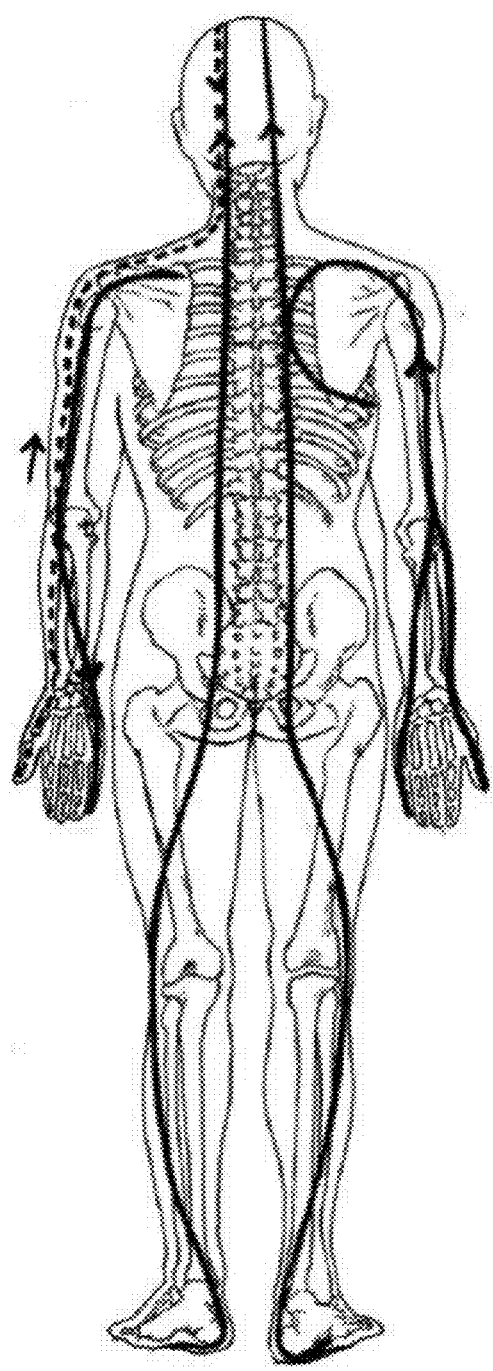
Figure 14:
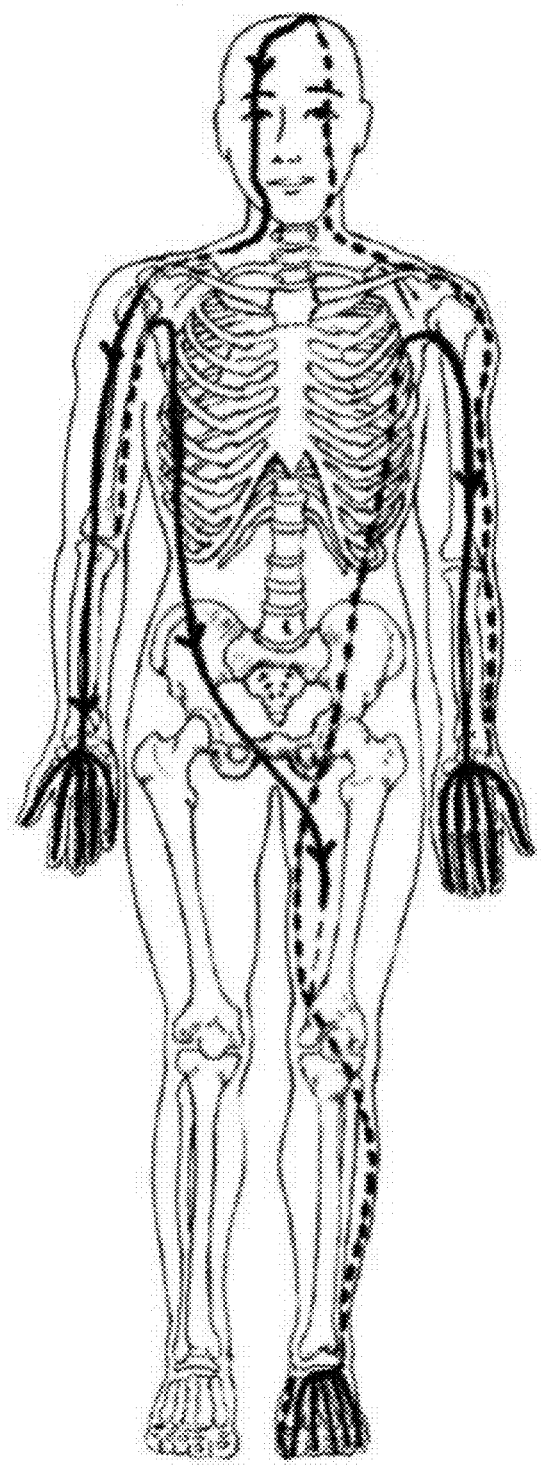

As can be seen by FIGS. 13A, 13B, and 14, energy flow in the body takes many directions. There is also a daytime and evening general energy direction that occurs naturally in the body. In the daytime the flow travels from the feet up the front of the body and down the back. This is called ascending energy. In the evening when the body is ready to rest in sleep the energy flow should reverse and flow from the feet up the back and down the front of the body. This is called descending energy. The proper flow of the ascending and descending energy is very important to good health. Disruption of these flows will effect sleep patterns and fatigue, and impair the proper function of other electromagnetic current lines.

Figure 15A:
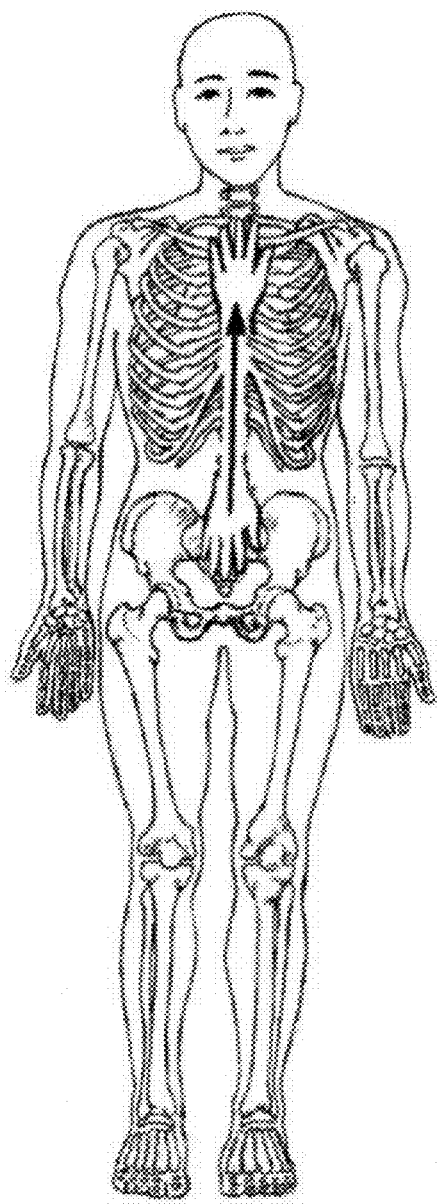
FIG. 15A shows ascending energy flow through a human body.

FIG. 15A shows the ascending energy (flow from feet to head) being stimulated by the hands. The left hand fingers toward the head and the right hand fingers toward the feet are placed on the mid-line of the body. To achieve the same effect with the present invention, a first magnetic device is placed on the navel with the directional arrow pointing down, and a second magnetic device is placed on the coccyx tip with the directional arrow facing up.

Figure 15B:
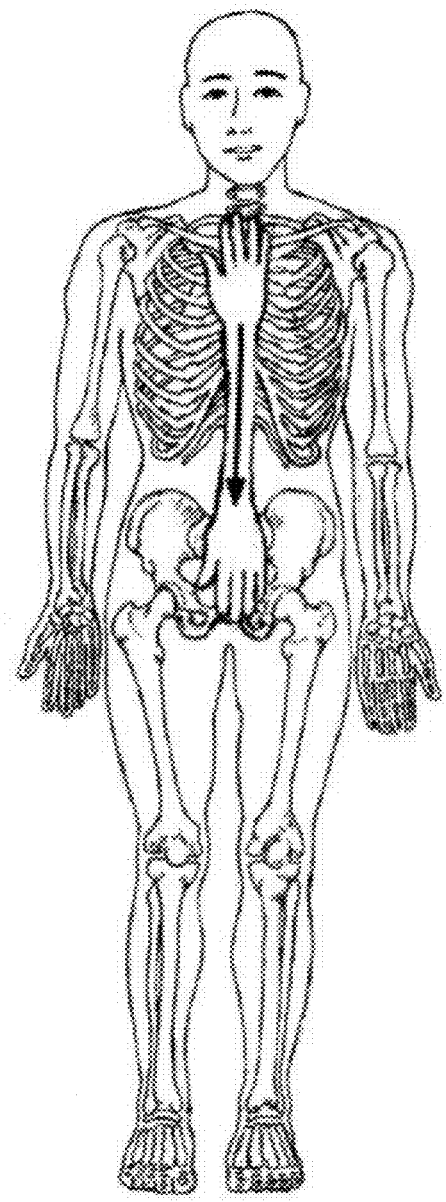
FIG. 15B shows descending energy flow through a human body.

In FIG. 15B, the opposite energy flow is being addressed. The hands are positioned with the right hand on the upper portion of the body with the fingers toward the head and the left hand positioned on the lower part of the body with fingers toward the feet to address the descending energy. To address this energy, the first magnetic device is placed on the navel with the directional arrow facing up, and the second magnetic device is on the coccyx tip with the directional arrow facing down.

Energy can also become pooled in a certain area of the body. These areas of stagnation can be located by a hardness that is felt just under the skin. The area can be small (¼ inch) or quite large (3-4 inches). These areas are strongly affected by the direction of hand placement on the body or the direction of the alignment markers on the magnetic devices disclosed in the present invention. Thus, hand placement to correct energy flow problems correlates to the alignment markers on the magnetic devices disclosed in the present invention.

The present invention preferably has many valuable uses in dentistry because the teeth can have a huge impact on the health of an individual. Many electromagnetic lines run through the teeth. So when the teeth have issues, it will affect the lines or flows that pass through them causing disruption.

Figure 16:
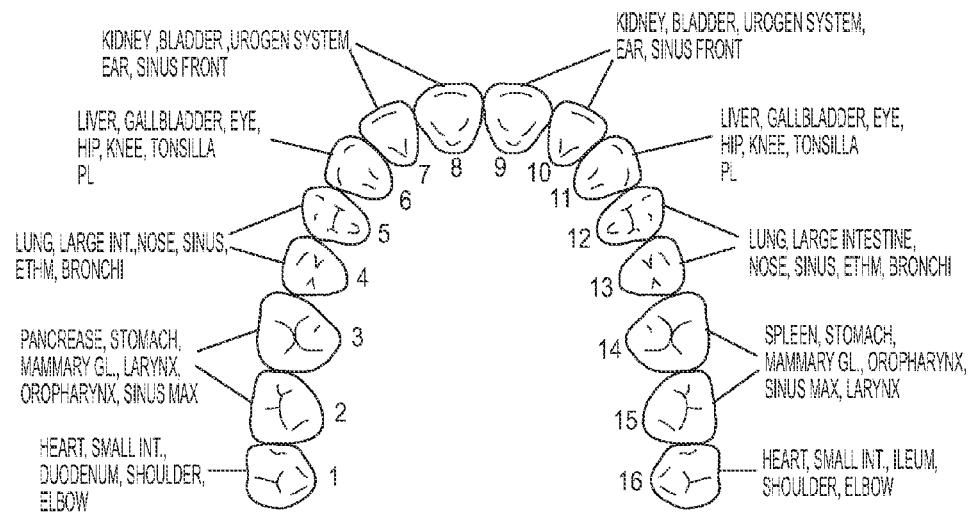
FIGS. 16 and 17 show the relationship between the teeth and parts of the human body.

We can see how teeth impact the health of an individual when we examine the connection tooth #3, the first molar on the upper right side of the mouth, has with the rest of the body. Referring to FIG. 16, a serious problem with this tooth can affect the pancreas, small intestine, larynx, mammary gland on the right breast, stomach, medial ankle, anterior knee, anterior hip, TMJ on the right side of the jaw, maxillary sinus, tongue, and thyroid.

Figure 17:
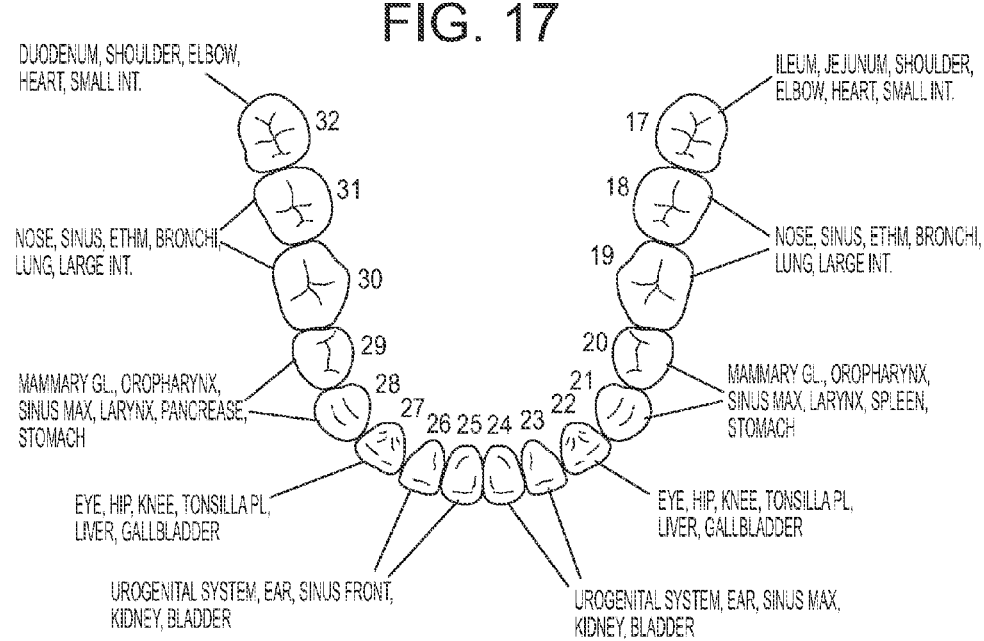

Another example is tooth #25, the central incisor right lower. Referring to FIG. 17, serious problems with this tooth could affect the adrenal glands, nose, sphenoid sinus, frontal sinus, sacrao-coccygeal joint, posterior hip and knee, kidney on the right side, bladder, genitor-urinary, ovaries, uterus, testicles, prostate, and the right ear.

A relatively new discovery in dentistry is a condition that can occur when a tooth is extracted, called a cavitation or "NECO" (Neuralgia Inducing Cavitational Osteonecrosis) lesion. The term NECO was given because some specialists feel that this dental issue could be responsible for Trigeminal Neuralgia as well as other types of facial pain.

A cavitation is a hole in the bone, which usually occurs where a tooth has been removed. In an X-ray, this area will show up as a shadow of a tooth. After a tooth is extracted, some feel that the membrane of the tooth remains behind so that the bone at this location never fills in. It may also be caused by the lines or flows that feed that particular tooth. If the lines or flows are experiencing a weakened condition, the space left behind after an extraction will have difficulty healing. The result is a spongy spot in the jaw at the extraction site. Other traumas can also cause cavitations.

There are many health dangers associated with a cavitation. These areas become breeding grounds for bacteria and the toxins they give off. They can also harbor mercury, and are very detrimental to the balanced flow of the energy lines, acting almost like a "leak" in the bioelectrical energy of the body. It is almost impossible to completely correct weakened flows that run through a cavitation or NECO lesion, which makes them a silent cause of recurring health issues.

Prior to the present invention, surgery would have been the recommended course to handle a cavitation. Surgery is very costly, painful, and can leave behind scar tissue which carries its own set of health issues. In one embodiment of the present invention, a magnetic device may be placed on an area of the face that correlates with cavitation location in the jaw so that the cavitations or NECO lesions can be stimulated to heal.

Muscle Response Testing is used to determine 1) the proper location for the magnetic device on the face, 2) the direction of the arrow on the magnetic device, and 3) the amount of time needed for placement of the magnetic device. In one embodiment, the average time the magnetic device will be worn on the face to correct a cavitation is around 56 hours.

The methods disclosed herein may also be used for other dental issues. When magnetic devices are placed near location #18 (FIG. 8A) on the thumb, it can calm the gag reflex some experience during dental work. It may also help speed healing with any type of dental procedure by addressing the energy lines that affect the particular area of the mouth that is being worked on. These placements are very individualized and are not necessarily placed at the site of the actual dental work. As an example, a person who received a root canal may wear the magnetic device on location #20 (FIG. 8A) on the forehead. This facilitates healing, which, in turn, helps with pain and discomfort. The patient is able to go about their business as through dental work had not been performed. This type of placement would follow the same procedure that has been outlined herein for placement of devices on an individual.

The present invention may be used to treat patients having a wide variety of conditions and diseases as discussed in case studies 1-10 below.

Case Study #1. A young girl about 10 years old had a fear of the dark. Whenever the family would arrive home at night, she couldn't enter the house until lights were turned on. MRT was conducted to determine if the present invention would work to help her alleviate her phobia of the dark. Energy flows or lines are responsible for anything the body experiences; they are even responsible for phobias that individuals may have. To test the patient, she was asked to think about the dark, which weakened her deltoid muscle, registering as weakness in her arm when gentle pressure was applied. The patient was then told to hold one of the magnetic devices in her hand and she was asked to think about the dark. This time the deltoid muscle was strong, indicating that the present invention would help her overcome her fear of the dark. Once again, the patient was asked to think about her phobia and tested which contact points on her body showed weakness as described previously under the method. These would be the locations that affected the lines or flows responsible for the phobia.

Figure 18:
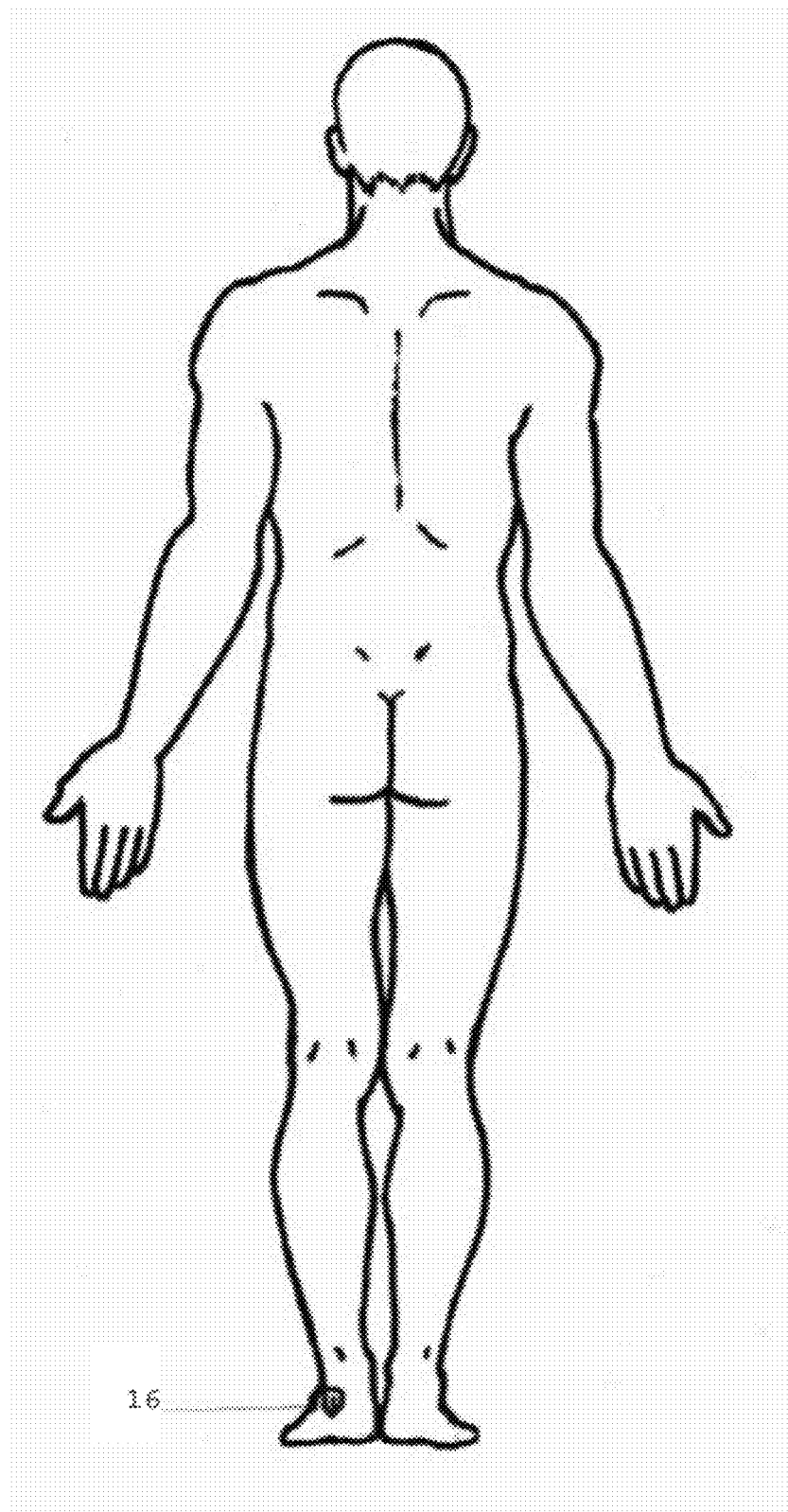
FIG. 18 shows a method of treating a patient, in accordance with one embodiment of the present invention.

Referring to FIG. 18, during MRT testing, through a process of elimination, it was discovered that the energy sphere or lock #16 on the outside of the left ankle was registering weakness when she thought about the dark. It was determined that only one device was needed because only one location made the deltoid muscle go weak, indicated by the arm weakening. Also, when the young patient held one device in her hand, her deltoid muscle was strong but when another was added, it weakened, indicating her body only needed one device placed in one location. The location would be the left #16 on the outside of the ankle.

The device was placed against the area and tested the strength of the deltoid by process of elimination as described in the method, it was determined that the arrow direction would be down. Then through asking the body verbal questions while muscle testing, it was determined that she would need to wear the device on the left #16 for 10 hours which, because of her age, and the fact that she was in school, she wore while she slept. Arrow direction would be down. Through MRT we determined the apparatus would be worn three nights in a row. The Result: Her fear of the dark is vastly diminished.

Case Study #2. A patient had not been feeling well for a few weeks and through muscle response testing it was determined that this was bacterial in origin. As with Case Study #1, MRT was conducted to determine which point on the body was the root of the problem. The location of the problem would show up as a weakness in the deltoid muscle reflected in the testing arm weakening when light pressure was gently applied, and the problem location was touched.

Figure 19:
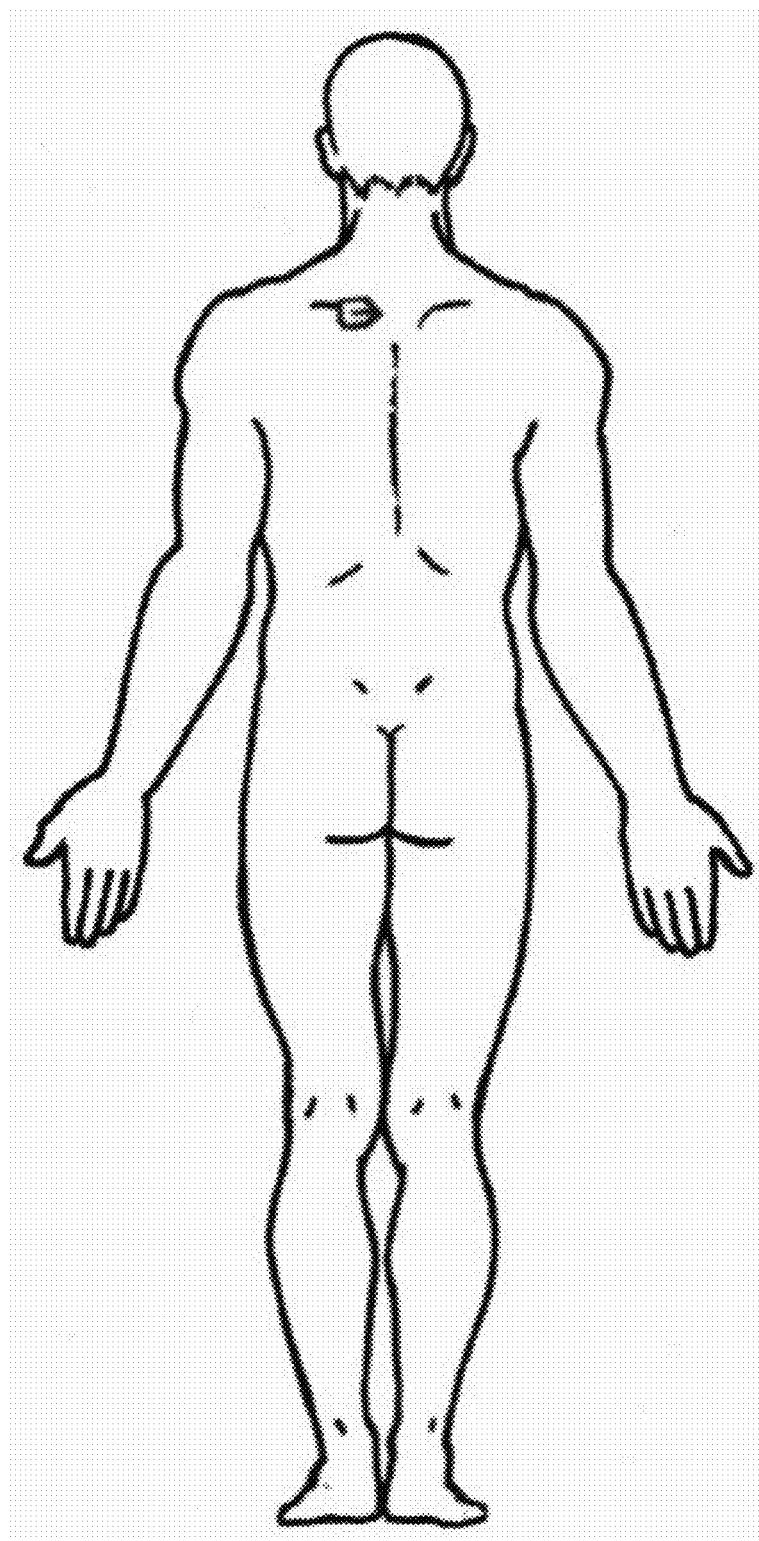
FIG. 19 shows a method of treating a patient, in accordance with one embodiment of the present invention.

The patient then held the magnetic device to see if the body would respond to the new therapy. The response was a strengthening of the arm when the weak area was touched while the individual held the apparatus. Then the number of devices needed was tested. The patient needed only one device because when two were placed in his hand, the patient's deltoid went weak, and only one location was found when points on the body were tested. Referring to FIG. 19, the location needed was the left #3 on the top of the shoulder blade close to the spine. This location fits with the prior test that indicated that the problem was bacterial in nature as the #3 point is considered the body's natural antibiotic. A test for arrow direction was conducted by moving the arrow on the #3 location until the arm registered strength. This happened when the arrow was toward the patient's right.

The test continued using verbal questions to determine the amount of time the patient would need to wear the device. The length of time was 10 hours and even though it did not have to be applied at a specific time (occasionally the time of application does matter as noted in the Chinese meridian clock) the patient wished to sleep with it on. When the patient woke up the next day, he reported that the symptoms he had been suffering with were gone.

Case Study #3. This case involved a tooth extraction that would possibly have led to a cavitation in the area due to the fact that the lines or flows that passed through that tooth were already showing signs of weakness or blockage. Cavitations or NECO lesions are caused by a lack of blood flow to the area of the extraction leaving the tissue in a necrotic state. In a sense it's a black hole. Since many of these energy lines run through the teeth, cavitations can cause problems along those lines or flows. These are very difficult to correct if the cavitation or NECO lesion is not addressed.

Figure 20:
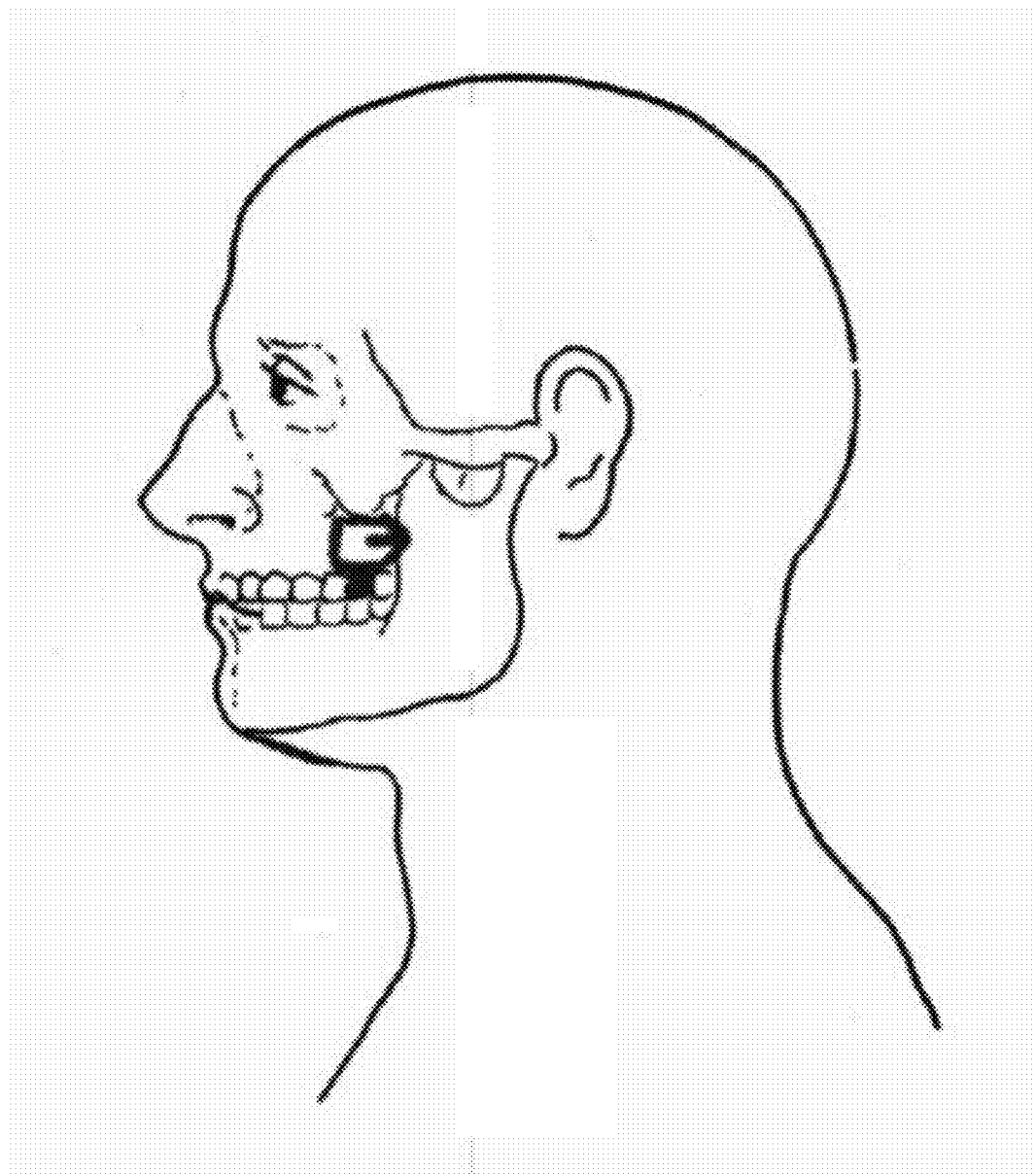
FIG. 20 shows a method of treating a patient, in accordance with one embodiment of the present invention.

Referring to FIG. 20, the tooth extracted was #15, the second molar. This tooth correlates with the parathyroid, tongue, maxillary sinus, left jaw TMJ, anterior hip, anterior knee, medial ankle joint, spleen, stomach, left breast, bladder, and pancreas. The area was MRT by pointing to different locations on the outside of the mouth close to the extraction site until the deltoid weakened. When the weakened area was located, the apparatus was applied over the location on the outside of the mouth.

The direction of the arrow was then tested, and it was to point toward the back of the head. Through verbal questions it was discovered that the device was to be left on for a total of 59 hours straight (there are cases where the time can be broken up). When examined three days later, the area of extraction was almost totally healed, the patient felt better, and the patient reported that her skin was healthier. Due to the fast healing of the area, pain was kept to a minimum as well.

Figures 21A, 21B:
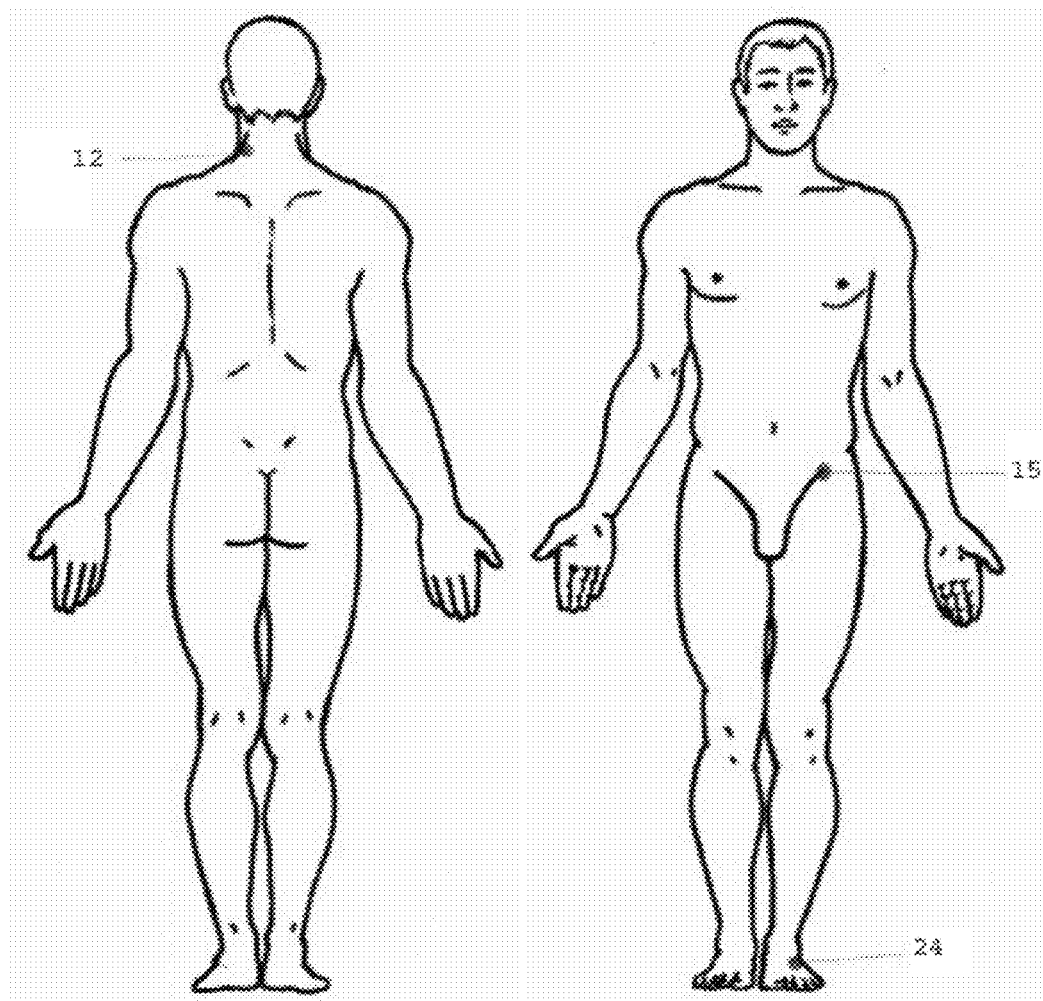
FIGS. 21A-21B show a method of treating a patient, in accordance with one embodiment of the present invention.

Case Study #4. A patient had a pinched nerve in his neck. He was unable to move his head to the left or the right. The pain was so intense that it was to the point of nausea. This went on for about three weeks while other methods were tried unsuccessfully. The patient was tested to see if the new method would work for him and it was determined that it would, by the muscles of his arm registering strength. The patient was then tested to see which locations of the body would be used to correct his problem. Referring to FIGS. 21A and 21B, three locations were determined through MRT, which were the area of the #12 on the left side of the neck, the #15 on the left side of the groin area, and the #24 on the top of the left foot. At each location, the arrow direction was then tested and it was determined that the arrows at all three locations would be facing to the right of the individual. The patient was then tested to determine length of treatment and it was determined that all three devices were to be applied at the same time and were to stay on together for a total of 12 hours. It was also determined through MRT that at the end of the 12 hours the #15 and #24 were to be removed and the #12 was to remain on the neck for another 12 hours. Before the devices were placed on the body, the patient could not move his head to the right or left. After treatment, the patient could freely move his head and the pain had almost entirely disappeared. He reported being about 70-80% better than the day before. A second set of devices were recommended to reach 100% correction, but the patient felt so good he never applied them.

Case Study #5. A 28 year old patient was having a lot of health problems after he was in a serious car accident. The testing point for the vagus nerve was determined to be very weak, which is an indicator for major structural problems, probably as a result of the car accident. These structural problems were affecting the lines or flows for the gallbladder, umbilicus, and bladder energies. He was experiencing most of the symptoms that these blocked lines will manifest.

Figures 22A, 22B:
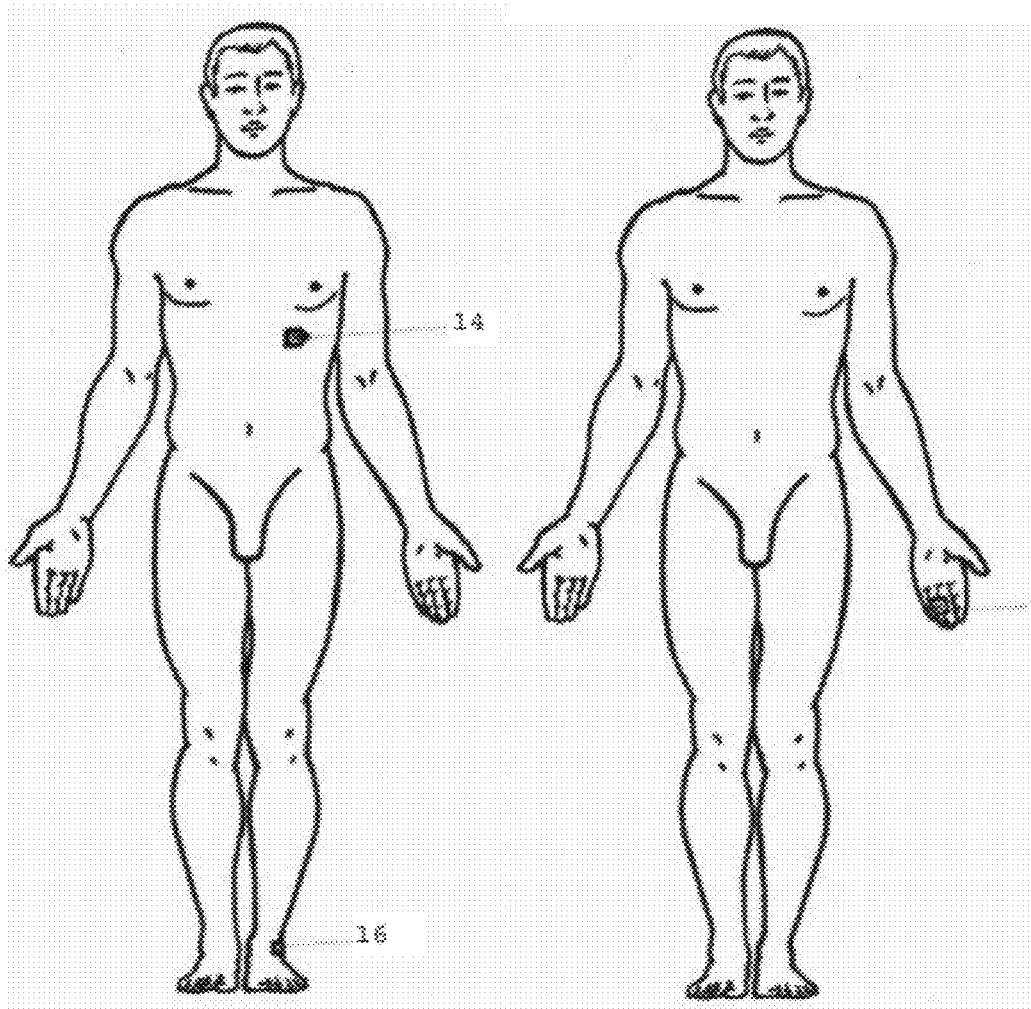
FIGS. 22A-22C show a method of treating a patient, in accordance with one embodiment of the present invention.

After identifying the problem lines or flows, MRT was used to determine which lines needed to be addressed first. Through MRT, it was determined that the gallbladder line needed to be worked on first. This determination was made by verbal questions. It was also determined that two locations were to be used to restore flow to the gallbladder line. Referring to FIGS. 22A-22B, the devices were placed on the #14 located along the rib cage on the left side of the body, and the #16 located on the left outer ankle. MRT was conducted to determine that the arrow on the #14 was to be pointing to the individual's left, and on the #16, the arrow pointed down.

Both apparatuses were to be applied to the body at the same time and were to be left on together for a total of 10 hours. After the 10 hour placement was completed, the #16 was to be removed, but the #14 was to stay on another 10 hours by itself. After the #14 was worn on the body for a total of 20 hours, it was to be removed also. It was determined through MRT that the patient would need a second placement series, but a space of a week would be needed between the two placement series. The patient reported, in the seven days between placements, that he felt a bit better every day. He reported that it was the first time he felt better since the accident.

Figure 22C:
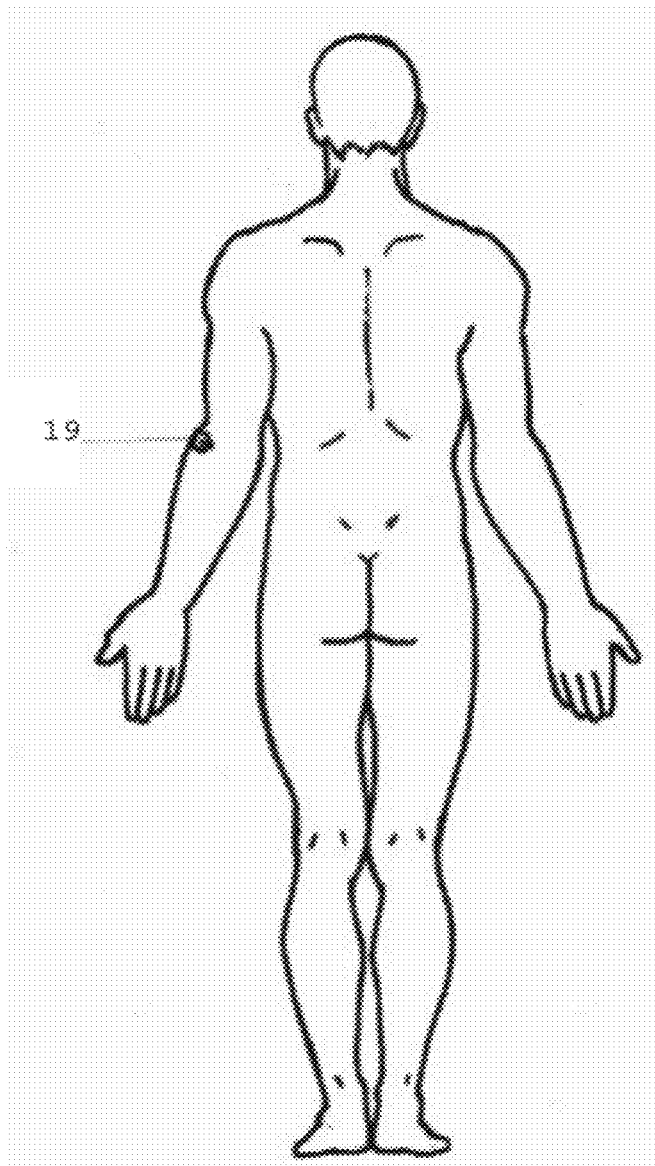

Case Study #5—Second Round of Placements. The second round of placements was necessary to balance out a flow called the 5$^{th}$ stratum, and the umbilicus line. Referring to FIGS. 22B and 22C, once again, two devices would be needed, with one placed on the left #19 on the arm by the elbow, and the other on the left ring finger. The arrow on the device placed on the left #19 would be facing to the right of the patient as would the device placed on the ring finger. It was determined that the #19 was to be placed on the body first and would remain on the body alone for a total of 10 hours. After the completion of the 10 hours another apparatus was added to the finger. Both devices were to stay on together for another 10 hours. When the 10 hours were complete, the ring finger device was to be removed, and the device on the #19 was to remain on for another 5 hours. This second set brought the patient's vagus point into complete balance, as indicated by the deltoid muscle registering strength when the point was tested. At the end of treatment, it was determined that the patient was symptom-free.

Figure 23:
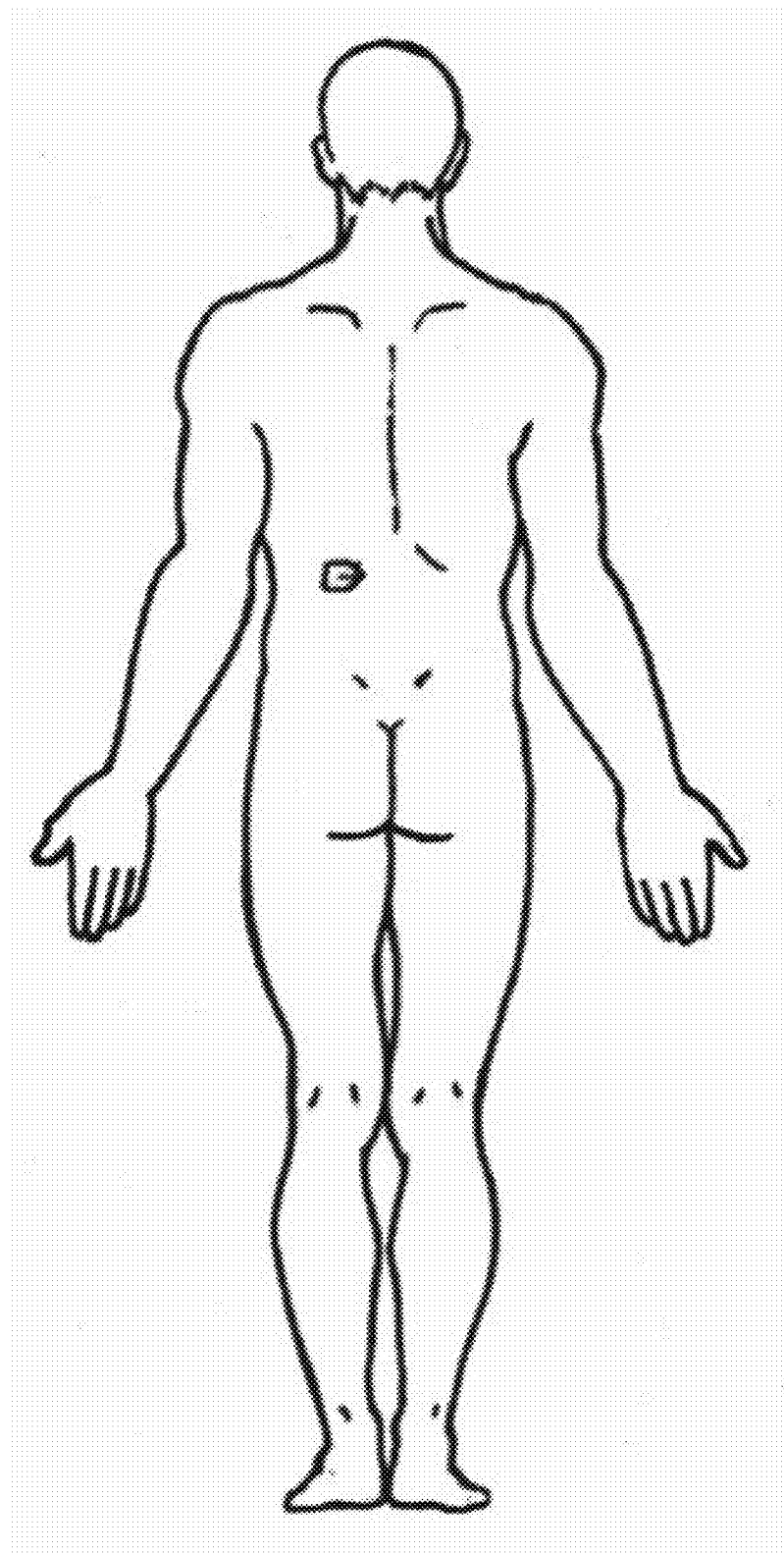
FIG. 23 shows a method of treating a patient, in accordance with one embodiment of the present invention.

Case Study #6. The patient was suffering from flu-like symptoms. Referring to FIG. 23, it was determined that one device would be needed, and it was to be placed on the left #23, with the arrow pointing to the individual's left. The apparatus was to be left on the left #23 for 3-4 hours (with influenza it can stay on as long as 9 hours). In three hours all symptoms of influenza were gone.

Figure 24:
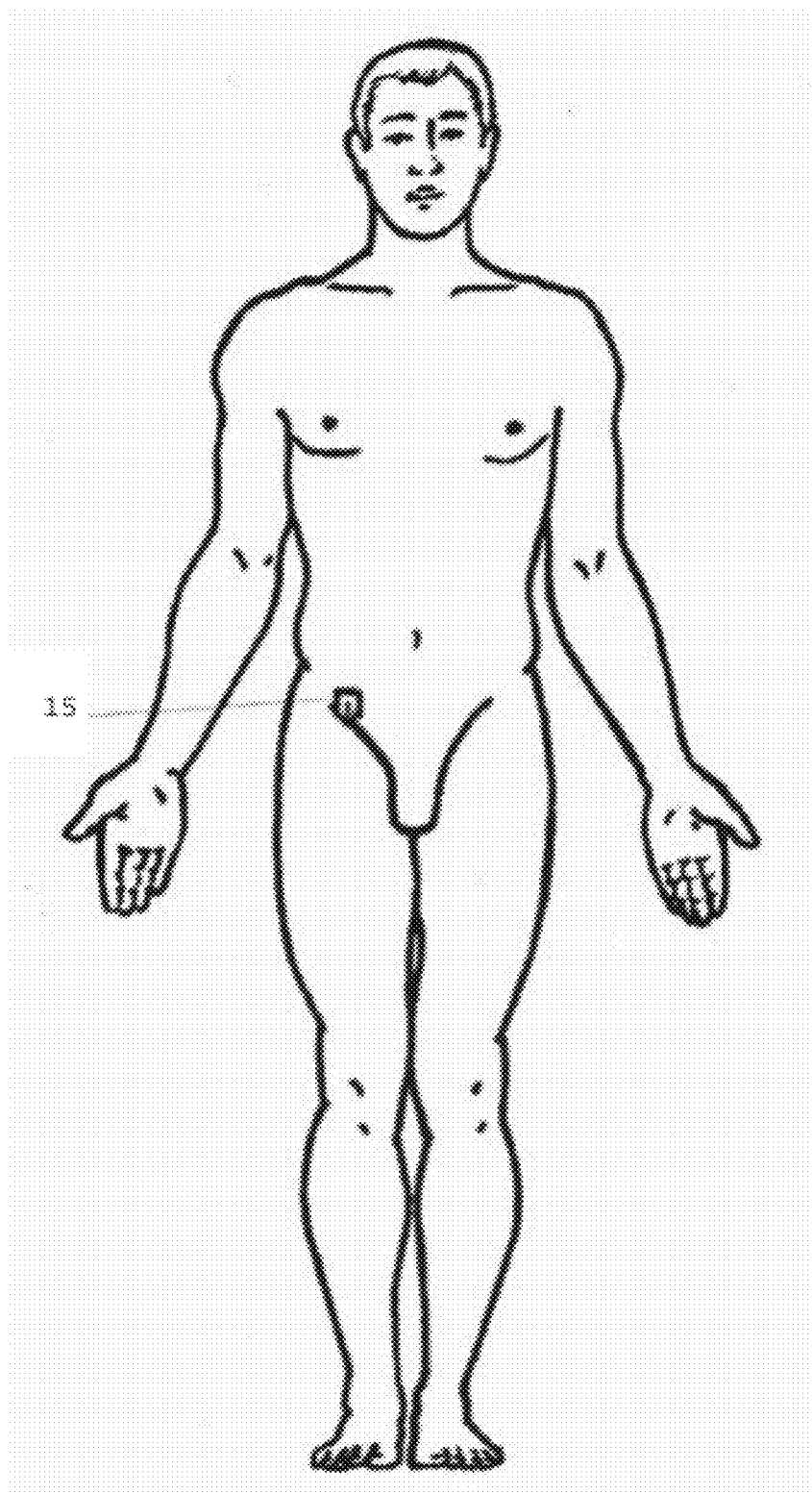
FIG. 24 shows a method of treating a patient, in accordance with one embodiment of the present invention.

Case Study #7. The patient was suffering from a stomach virus, experiencing diarrhea, and abdominal rumbling and discomfort. Referring to FIG. 24, MRT determined that a device needed to be placed on the right #15 with the arrow direction pointing down toward the feet. The apparatus was to be left on for about 5 or 6 hours. The patient started feeling better shortly after application of the device and by the time 5 hours had passed, the patient felt no symptoms of illness at all.

Figure 25:
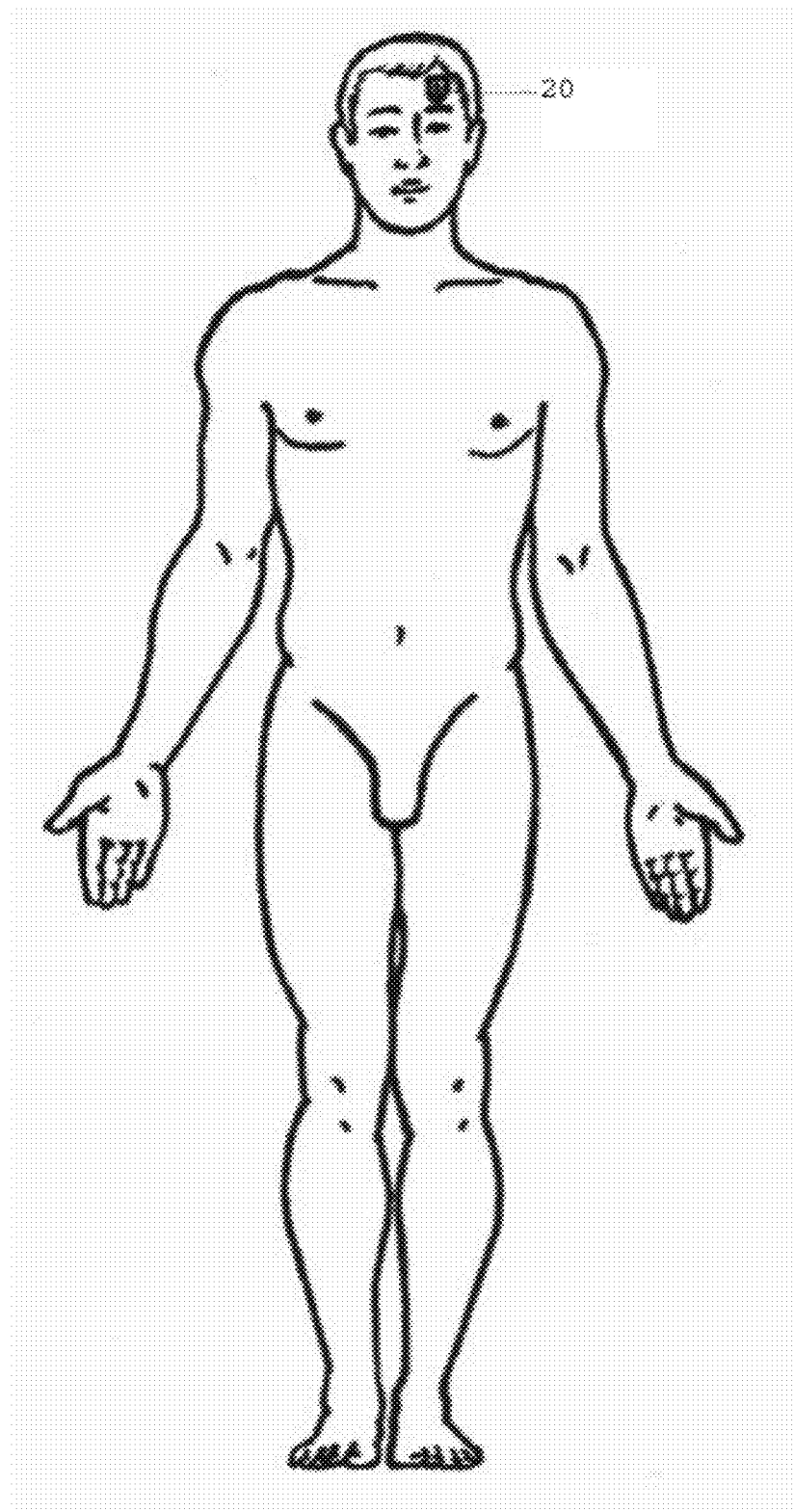
FIG. 25 shows a method of treating a patient, in accordance with one embodiment of the present invention.

Case Study #8. This case study involved a patient that needed a root canal procedure. Referring to FIG. 25, MRT testing indicated that the device should be placed on the forehead on the left #20 location. MRT was also conducted to determine whether the device or devices need to be placed on before, during, or after the procedure. It was determined through MRT that one device was to be placed prior to the dental procedure and left on until the procedure was completed, which facilitated the healing of the area and helped eliminate much of the discomfort experienced after the procedure. No pain medication of any kind was needed after the procedure, not even an aspirin.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for treating patients comprising:
   a first magnetic device including a set of four magnetic discs arranged in a square array, said four magnetic discs including two having negative magnetic poles lying in a first plane and two having positive magnetic poles lying in said first plane, wherein said two magnetic discs having negative magnetic poles extend along a first diagonal line and said two magnetic discs having positive magnetic poles extend along a second diagonal line that crosses said first diagonal line;
   a housing containing said four magnetic discs for maintaining said magnetic discs in said square array arrangement, said housing including an alignment marker for aligning said first magnetic device on a patient.

2. The system as claimed in claim 1, wherein said housing has a substantially flat top surface, a substantially flat bottom surface and a sidewall that extends between said top and bottom surfaces and around a perimeter of said housing, and wherein said alignment marker extends over said top surface of said housing.

3. The system as claimed in claim 2, wherein said sidewall of said housing has three sides that conform to said square array and one side including an obtuse angle defining an apex of said housing, and wherein said alignment marker has a leading end that intersects said apex.

4. The system as claimed in claim 3, wherein said housing includes a center marker on a top surface thereof that indicates a central location between said four magnetic discs.

5. The system as claimed in claim 1, further comprising:
a second magnetic device including a second set of four magnetic discs arranged in a square array, said second set of four magnetic discs including two having negative magnetic poles lying in a first plane and two having positive magnetic poles lying in said first plane, wherein said two magnetic discs having negative magnetic poles extend along a first diagonal line and said two magnetic discs having positive magnetic poles extend along a second diagonal line that crosses said first diagonal line;
a second housing containing said second set of four magnetic discs for maintaining said magnetic discs in said square array arrangement, said second housing including a second alignment marker for aligning said second magnetic device on a patient.

6. The system as claimed in claim 4, further comprising:
a case for storing said first and second magnetic devices;
a plurality of adhesive discs storable in said case; and
an instruction manual storable in said case.

7. An octapolar magnetic device comprising:
a set of four magnetic discs arranged in a square array, said four magnetic discs including two having negative magnetic poles lying in a first plane and two having positive magnetic poles lying in said first plane, wherein said two magnetic discs having negative magnetic poles extend along a first diagonal line and said two magnetic discs having positive magnetic poles extend along a second diagonal line that crosses said first diagonal line;
a non-metallic housing containing said four magnetic discs for maintaining said magnetic discs in said square array arrangement, said housing including an alignment marker for aligning said octapolar magnetic device on a patient.

8. The device as claimed in claim 7, wherein said housing has a substantially flat top surface, a substantially flat bottom surface and a sidewall that extends between said top and bottom surfaces and around a perimeter of said housing, and wherein said alignment marker extends over said top surface of said housing.

9. The device as claimed in claim 8, further comprising an adhesive device secured to said bottom surface of said housing.

10. The device as claimed in claim 9, wherein said four magnetic discs are sufficiently close that the magnetic induction produced by each of said magnetic poles has a significant magnitude at the location of each of the other of said magnetic poles, and wherein said four magnetic discs are sufficiently distant from other sources of magnetic induction that the magnetic induction field generated by said four magnetic discs is not substantially distorted.

11. The device as claimed in claim 7, wherein each of said four magnetic discs has two opposing end faces, one of said two end faces having a positive magnetic pole thereon and the other of said two end faces having a negative magnetic pole thereon, the positive magnetic pole end faces of two of said discs and the negative magnetic pole end faces of two of said discs being in said first plane, and the opposite magnetic pole end faces of two of said discs and the positive pole end faces of two of said discs being in a second plane, and wherein each of said magnetic discs is center charged.

12. A method of treating a patient comprising:
conducting muscle response testing on a patient for indentifying at least one location for treatment;
placing a magnetic device over the at least one location identified, said magnetic device including a set of four magnetic discs arranged in a square array, said four magnetic discs including two having negative magnetic poles lying in a first plane and two having positive magnetic poles lying in said first plane, wherein said two magnetic discs having negative magnetic poles extend along a first diagonal line and said two magnetic discs having positive magnetic poles extend along a second diagonal line that crosses said first diagonal line, and a housing containing said four magnetic discs for maintaining said magnetic discs in said square array arrangement, said housing including an alignment marker for aligning said magnetic device on the patient;
using said alignment marker on said housing for aligning said magnetic device over said at least one location on the patient for influencing energy flow in the patient.

13. The method as claimed in claim 12, further comprising:
conducting muscle response testing for identifying a second location for treatment;
placing a second magnetic device over the second location, said second magnetic device including a second set of four magnetic discs arranged in a square array, said four magnetic discs including two having negative magnetic poles lying in a first plane and two having positive magnetic poles lying in said first plane, wherein said two magnetic discs having negative magnetic poles extend along a first diagonal line and said two magnetic discs having positive magnetic poles extend along a second diagonal line that crosses said first diagonal line, and a second housing containing said second set of four magnetic discs for maintaining said magnetic discs in said square array arrangement, said second housing including a second alignment marker for aligning said second magnetic device on the patient;
using said second alignment marker on said second housing for aligning said magnetic device over said second location for influencing energy flow in the patient.

14. The method as claimed in claim 13, further comprising orienting said first alignment marker in a first direction on said patient and orienting said second alignment marker in a second direction that is different than said first direction.

15. The method as claimed in claim 13, wherein said first and second locations are selected from the group consisting of acupuncture points, electromagnetic lines, meridians, points used in traditional Chinese medicine, locations on the body used in Jin Shin Jyutsu, and locations on the body used in Ki-Iki Jutsu and Shiatsu.

* * * * *